US011066649B2

(12) United States Patent
Dubart Kupperschmitt et al.

(10) Patent No.: US 11,066,649 B2
(45) Date of Patent: Jul. 20, 2021

(54) METHOD FOR INDUCING HUMAN CHOLANGIOCYTE DIFFERENTIATION

(71) Applicants: INSERM (INSTITUT NATIONAL DE LA SANTÉ ET DE LA RECHERCHE MÉDICALE), Paris (FR); UNIVERSITE PARIS—SUD, Orsay (FR); UNIVERSITÉ DE RENNES, Rennes (FR)

(72) Inventors: Anne Dubart Kupperschmitt, Villejuif (FR); Anne Weber Benarous, Villejuif (FR); Anne Corlu, Rennes (FR); Noushin Dianat, Villejuif (FR)

(73) Assignees: INSTITUT NATIONAL DE LA SANTE ET DE LA RECHERCHE MEDICALE (INSERM), Paris (FR); UNIVERSITÉ PARIS-SACLAY, Gif-sur-Yvette (FR); UNIVERSITE DE RENNES, Rennes (FR)

( * ) Notice: Subject to any disclaimer, the term of this patent is extended or adjusted under 35 U.S.C. 154(b) by 171 days.

(21) Appl. No.: 15/125,596

(22) PCT Filed: Mar. 19, 2015

(86) PCT No.: PCT/EP2015/055811
§ 371 (c)(1),
(2) Date: Sep. 13, 2016

(87) PCT Pub. No.: WO2015/140257
PCT Pub. Date: Sep. 24, 2015

(65) Prior Publication Data
US 2016/0376557 A1    Dec. 29, 2016

(30) Foreign Application Priority Data

Mar. 19, 2014    (EP) .................................... 14305387

(51) Int. Cl.
*C12N 5/071* (2010.01)
*A61K 35/407* (2015.01)

(52) U.S. Cl.
CPC .......... *C12N 5/0679* (2013.01); *A61K 35/407* (2013.01); *C12N 5/0672* (2013.01); *C12N 2500/25* (2013.01); *C12N 2500/38* (2013.01); *C12N 2501/02* (2013.01); *C12N 2501/11* (2013.01); *C12N 2501/115* (2013.01); *C12N 2501/119* (2013.01); *C12N 2501/12* (2013.01); *C12N 2501/155* (2013.01); *C12N 2501/16* (2013.01); *C12N 2501/2306* (2013.01); *C12N 2501/305* (2013.01); *C12N 2501/385* (2013.01); *C12N 2501/395* (2013.01); *C12N 2501/415* (2013.01); *C12N 2501/727* (2013.01); *C12N 2501/998* (2013.01); *C12N 2501/999* (2013.01); *C12N 2506/02* (2013.01); *C12N 2506/14* (2013.01); *C12N 2506/45* (2013.01); *C12N 2533/54* (2013.01)

(58) Field of Classification Search
None
See application file for complete search history.

(56) References Cited

U.S. PATENT DOCUMENTS

| | | | | |
|---|---|---|---|---|
| 6,506,574 B1 * | 1/2003 | Rambhatla | ............. | C12N 5/067 435/15 |
| 2003/0170215 A1 * | 9/2003 | Tsang | .................. | A61L 27/3804 424/93.21 |
| 2011/0287539 A1 * | 11/2011 | Pauwelyn | .............. | C12N 5/067 435/377 |
| 2012/0301460 A1 * | 11/2012 | Bao | ...................... | A61K 9/0019 424/133.1 |

FOREIGN PATENT DOCUMENTS

| | | | | |
|---|---|---|---|---|
| WO | 2008/156667 A1 | 12/2008 | | |
| WO | WO 2012/025725 | * | 3/2012 | |
| WO | WO-2012089669 A1 * | 7/2012 | ........... | C12N 5/0696 |

OTHER PUBLICATIONS

Franchitto et al., "Recent Advances on the mechanisms regulating cholangiocyte proliferation and the significance of the neuroendocrine regulation of cholangiocyte pathophysiology", Annals of Translational Medicine, 2012, 1(3):27, pp. 1-13.*
Nakamura et al., "Feeder-Free and Serum-Free Production of Hepatocytes, Cholangiocytes, and Their Proliferating Progenitors from Human Pluripotent Stem Cells: Application to Liver-Specific Functional and Cytotoxic Assays", Cellular Reprogramming, 2012, vol. 14, No. 2, pp. 171-185.*
Nagata et al., "Oncostatin M, an lnterleukin-6 Family Cytokine, Upregulates Matrix Metalloproteinase-9 Through the Mitogen-Activated Protein Kinase Kinase-Extracellular Signal-Regulated Kinase Pathway in Cultured Smooth Muscle Cells", Arterioscler. Thromb. Vase. Biol., 2003, vol. 23, pp. 588-593.*
Alpini et al., "Bile Acid Feeding Increased Proliferative Activity and Apicale Bile Acid Transporter Expression in Both Small and Large Rat Cholangiocytes", Hepatology 2001, vol. 34, pp. 868-876.*

(Continued)

*Primary Examiner* — Laura Schuberg
(74) *Attorney, Agent, or Firm* — W&C IP

(57) ABSTRACT

The invention relates to a method for inducing human cholangiocyte differentiation of progenitor cells called hepatoblasts. More specifically, the invention relates to a method for differentiating hepatoblasts to cholangiocytes by culturing said hepatoblasts with a particular medium having interleukin-6 (IL-6) activity. The differentiation method can specifically induce cholangiocyte differentiation from hepatoblasts, and the human cholangiocytes differentiated according to the invention may be useful for drug discovery for treatment of cholangiopathies and bioengineered livers.

15 Claims, 1 Drawing Sheet

(56) References Cited

OTHER PUBLICATIONS

Figure 1:
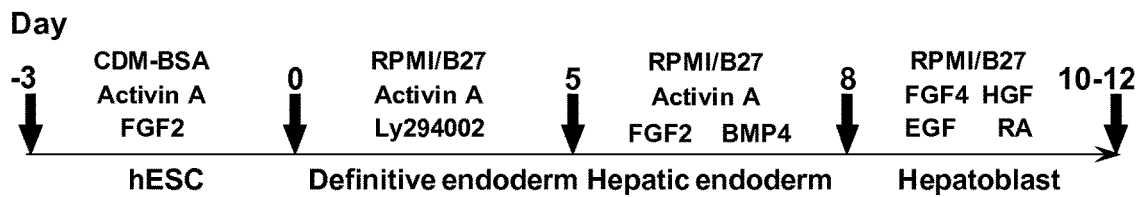
Figure 1:
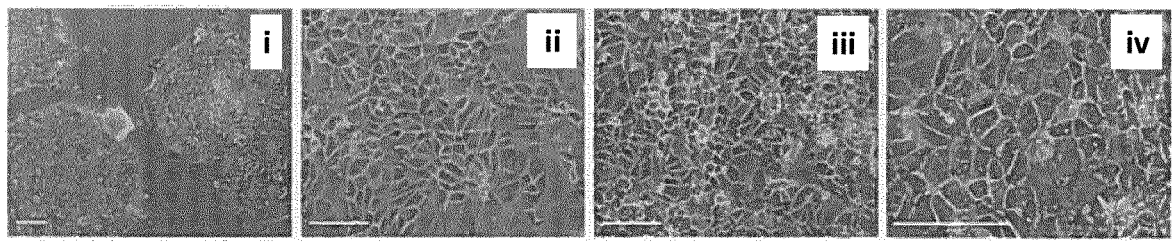

Tanaka et al., "Liver stem/progenitor cells: their characteristics and regulatory mechanisms", The Journal of Biochemistry, 2011, 149(3), pp. 231-239.*

Touboul et al, "Generation of Functional Hepatocytes from Human Embryonic Stem Cells Under Chemically Defined Conditions that Recapitulate Live Development", Hepatology 2010, vol. 51, pp. 1754-1765.*

Klausen et al., "Oncostatin M and Interleukin 6 inhibit cell cycle progression by prevention of p27kip1 degradation in HepG2 cells", Oncogene, 2000, vol. 19, pp. 3675-3683. (Year: 2000).*

Boileau et al., "Regulation of Extrathymic T Cell Development and Turnover by Oncostatin M", The Journal of Immunology, 2000, vol. 164, pp. 5713-5720. (Year: 2000).*

Breton et al., "Structure, stability and biological properties of a N-terminally truncated form of recombinant human interleukin-6 containing a single disulfide bond", Eur. J. Biochem., 1995, vol. 227, pp. 573-581. (Year: 1995).*

Dianat et al., "Human Pluripotent Stem Cells for Modelling Human Liver Diseases and Cell Therapy", Current Gene Therapy, 2013, vol. 13, No. 2, pp. 120-132. (Year: 2013).*

Matsumoto et al., "Human Biliary Epithelial Cells Secrete and Respond to Cytokines and Hepatocyte Growth Factors In Vitro: Interleukin-6, Hepatocyte Growth Factor and Epidermal Growth Factor Promote DNA Synthesis In Vitro", Hepatology, 1994, vol. 20, pp. 376-382. (Year: 1994).*

M Blouin: "Specialization Switch in Differentiating Embryonic Rat Liver Progenitor Cells in Response to Sodium Butyrate", Experimental Cell Research, vol. 217, No. 1, Mar. 1, 1995, pp. 22-30.

Shiojiri N et al: "Differentiation of functional hepatocytes and biliary epithelial cells from immature hepatocytes of the fetal mouse in vitro", Anatomy and Embryology, Springer International, Berlin, DE, vol. 187, No. 3, Mar. 1, 1993, pp. 221-229.

Noushin Dianat et al: "Generation of functional cholangiocyte-like cells from human pluripotent stem cells and HepaRG cells", Hepatology, vol. 60, No. 2, Jun. 20, 2014, pp. 700-714.

* cited by examiner

A

B

METHOD FOR INDUCING HUMAN CHOLANGIOCYTE DIFFERENTIATION

FIELD OF THE INVENTION

The invention relates to a method for inducing human cholangiocyte differentiation of progenitor cells called hepatoblasts. More specifically, the invention relates to a method for differentiating hepatoblasts to cholangiocytes by culturing said hepatoblasts with a particular medium having interleukin-6 (IL-6). The differentiation method can specifically induce cholangiocyte differentiation from hepatoblasts, and the human cholangiocytes differentiated according to the invention may be useful for treatment of cholangiopathies.

BACKGROUND OF THE INVENTION

In the early stages of liver organogenesis, the major components of hepatic parenchyma are hepatic progenitor cells (hepatoblasts, HB), which can differentiate into hepatocytes and cholangiocytes. Cholangiocytes are biliary epithelial cells that line the intra- and extra-hepatic ducts of the biliary tree. Around the eighth week of gestation in humans, hepatoblasts in the vicinity of the portal mesenchyme form a single layer ring of cells called the "ductal plate", which give rise to cholangiocytes.[1] The ductal plate is also assumed to be the compartment of hepatic stem cells in fetal and neonatal livers, although this is still controversial.[2-4] One of the first pathways that prime biliary commitment and formation of the ductal plate is the NOTCH pathway: JAGGED1-positive mesenchymal cells in periportal areas interact with adjacent NOTCH2-positive hepatoblasts and induce cholangiocyte differentiation. NOTCH pathway activation induces SOX9 expression, which is the most specific and earliest marker of biliary cells in developing liver and controls bile duct morphogenesis.[1] Sal-like protein 4 (SALL4) is also reported as a key transcription factor controlling the lineage commitment of hepatoblasts, not only by inhibiting their differentiation into hepatocytes but also by driving their differentiation toward cholangiocytes.

The main physiological function of cholangiocytes is to actively regulate bile composition by modification of hepatocyte-derived bile components through a series of secretory and reabsorptive events. In addition to their role in the modification of ductal bile, cholangiocytes participate in the detoxification of xenobiotics.[5] They are also the primary targets of injury in a variety of cholestatic liver diseases, ranging from inherited disorders (Alagille syndrome and cystic fibrosis) or autoimmune cholangitis to primary biliary cirrhosis which represent the main indication for liver transplantation in pediatrics.[6] Despite the physiological and pathological importance of cholangiocytes, their limited number (3% of the total liver mass) and their intrahepatic localization have limited the development of in vitro cell models in order to gain molecular insights into their function. At present, few human cholangiocyte cell lines are available. They are derived from either cholangiocarcinoma or normal cells immortalized by SV40,[7] and most of the cells studied in vitro are derived from rat cholangiocytes.[8] However, important dissimilarities exist between rodent and human models: in particular, only human, but not rodent, small cholangiocytes express cystic fibrosis transmembrane conductance regulator (CFTR).[9]

Pluripotent stem cells, which can differentiate into various cell types and display an infinite ability to proliferate, have appeared as an alternative and reproducible source of differentiated cells with therapeutic interest.[10] To date, numerous studies have focused on the development of efficient protocols to generate hepatocyte-like cells, and several groups have already generated hepatocyte-like cells from hESCs and hiPSCs in vitro.

However the question remains whether hepatic progenitors generated via different protocols are able to generate cholangiocytes.

SUMMARY OF THE INVENTION

In a first aspect, the invention relates to a method for inducing human cholangiocyte differentiation comprising the steps of:

(i) providing a population of human hepatoblasts (hHB); and (ii) culturing the population of hHB in at least one cholangiocyte induction medium to produce a population of cholangiocytes, wherein said cholangiocyte induction medium is a chemically defined medium (CDM) which has interleukin-6 activity.

In a second aspect, the invention relates to a population of human cholangiocytes produced by a method of the invention.

In a third aspect, the invention relates to a population of human cholangiocytes of the invention, for use in a method of treatment of the human body.

In a fourth aspect, the invention relates to a population of human cholangiocytes of the invention, for use in the treatment of a patient with a cholangiopathy.

In a fifth aspect, the invention relates to a method of screening for a compound useful in the treatment of a cholangiopathy comprising the steps of:

(c) contacting a population of cholangiocytes produced by a method of claim 9 with a test compound, and;

(d) determining the effect of the test compound on said cholangiocytes.

DETAILED DESCRIPTION OF THE INVENTION

The present approach recapitulates the key stages of liver development and enabled to stepwise differentiate hESCs and hiPSCs into definitive endoderm cells, hepatic progenitors and cholangiocyte-like cells in a fully defined medium without feeder cells or serum.

The inventors thus developed a robust and efficient method for differentiating pluripotent stem cells, hESC and hiPSC, and HepaRG-derived hepatic progenitors (hepatoblasts) to differentiate further along the cholangiocytic lineage and reported a new approach, which drive differentiation of pluripotent stem cells toward the cholangiocytic lineage using feeder-free and defined culture conditions. After differentiation into hepatic progenitors, pluripotent stem cells were differentiated further into cholangiocytes using growth hormone, epidermal growth factor, Interleukin-6 and then sodium taurocholate. These conditions also allowed us to generate cholangiocytes from HepaRG-derived hepatoblasts. Pluripotent stem cells- and HepaRG-derived cholangiocyte-like cells expressed markers of cholangiocytes including Cytokeratin 7 and Osteopontin, and transcription factors SOX9 and Hepatocyte nuclear factor 6. The cells also displayed specific proteins important for cholangiocyte functions including cystic fibrosis transmembrane conductance regulator, secretin receptor and nuclear receptors. They formed primary cilia and also responded to hormonal stimulation by increase of intracellular Ca2+. The inventors also demonstrated by integrative genomics that the expression of genes, which signed pluripotent stem cells- or HepaRG-cholangiocytes separates hepatocytic lineage from cholangiocyte lineage. When grown in a 3D matrix, cholangiocytes developed epithelial/apicobasal polarity and formed functional cysts and biliary ducts.

Methods for Inducing Differentiation of the Invention

In a first aspect, the invention relates to a method for inducing human cholangiocyte differentiation comprising the steps of:
(i) providing a population of human hepatoblasts (hHB); and
(ii) culturing the population of hHB in at least one cholangiocyte induction medium to produce a population of cholangiocytes, wherein said cholangiocyte induction medium is a chemically defined medium (CDM) which has interleukin-6 (IL-6) activity.

As used herein, the term "population" refers to a population of cells, wherein the majority (e.g., at least about 60%, preferably at least about 70%, more preferably at least about 80%) of the total number of cells have the specified characteristics of the cells of interest (e.g. a population of human hepatoblasts comprises at least about 60%, preferably at least about 70%, more preferably at least about 80% of cells which have the hepatic functions and which express the markers typically expressed by human hepatoblasts listed below).

As used herein, the terms "hepatoblasts" (HB) or "hepatic progenitor cells" are used herein interchangeably. They refer to cells that are capable of expressing characteristic biochemical markers, including but not limited to Alpha-fetoprotein (AFP), Albumine (Alb), Cytokeratin 19 (CK19), Ep-CAM and Hepatocyte nuclear factor 4alpha (HNF4alpha). Such cells can differentiate into either hepatocytes or cholangiocytes and express markers of both lineages (i.e. as above-mentioned CK19 which is a specific marker of cholangiocytes; HNF4 alpha and AFP which are specific markers of hepatocytes). As described below, HB may be derived from pluripotent stem cells, from HepaRG, from fetal liver or directly obtained from other cell types by redirected differentiation.

As used herein, the term "marker" refers to a protein, glycoprotein, or other molecule expressed on the surface of a cell or into a cell, and which can be used to help identify the cell. A marker can generally be detected by conventional methods. Specific, non-limiting examples of methods that can be used for the detection of a cell surface marker are immunocytochemistry, fluorescence activated cell sorting (FACS), and enzymatic analysis but also RT-PCR and molecular biology methods to detect mRNA of the protein.

As used herein, the term "cholangiocytes" refers to the epithelial cells of the bile ducts. Cholangiocytes are biliary epithelial cells, which, like hepatocytes, originate from hepatoblasts during embryonic development. The morphology of cholangiocytes as well as their functions varies along the biliary trees. Cholangioctes in the small interlobular bile ducts are cuboidal cells but become columnar and mucus secreting in larger bile ducts approaching the extrahepatic portion. In the healthy liver, cholangiocytes contribute to bile secretion via net release of bicarbonate and water. Several hormones and locally acting mediators are known to contribute to cholangiocyte fluid/electrolyte secretion. These include secretin, acetylcholine, ATP, and bombesin. As the primary bile flows through the bile ducts, its composition is regulated by the intrahepatic bile duct epithelium that reabsorbs fluids, aminoacids, glucose and bile acids, while secreting water and electrolytes and IgA. Cholangiocytes refer to cells that are capable of expressing characteristic biochemical markers, including but not limited to CFTR, G-protein coupled bile acid receptor 1 (TGR5), Aquaporin-1 (AQP1), SOX9, Secretin receptor (SCTR), JAG1, CK7, CK19, CK18, Osteopontin (OPN), HNF6 and HNF13.

As used herein, the term "chemically defined medium" (CDM) refers to a nutritive solution for culturing cells which contains only specified components, preferably components of known chemical structure. A chemically defined medium is a serum-free and feeder-free medium. As used herein, "serum-free" refers to a culture medium containing no added serum. As used herein, "feeder-free" refers to culture medium containing no added feeder cells. The term feeder-free encompasses, inter alia, situations where hepatoblasts are passaged from a culture without feeders into a culture medium without added feeders even if some of the feeders from the first culture are present in the second culture.

In one embodiment, the cholangiocyte induction medium comprises IL-6.

Accordingly, the invention relates to a method for inducing human cholangiocyte differentiation comprising the steps of:
(i) providing a population of human hepatoblasts (hHB); and
(ii) culturing the population of hHB in at least one cholangiocyte induction medium to produce a population of cholangiocytes, wherein said cholangiocyte induction medium is a chemically defined medium (CDM) comprising IL-6.

As used herein, the term "Interleukin-6" (IL-6) refers to a polypeptide involved in the regulation of immune responses such as lymphocyte differentiation. IL-6 is well known in the art and is also known as B cell-stimulating factor 2 (BSF-2) or interferon beta-2 (IFNB2). The term also refers to any of the naturally-occurring forms of the IL-6, or variants thereof that maintain IL-6 activity (e.g. within at least 50%, 80%, 90% or 100% activity compared to wild type IL-6 as measured by methods known in the art). In some embodiments, variants have at least 90% amino acid sequence identity across their whole sequence compared to the naturally occurring IL-6 polypeptide. The naturally occurring human IL-6 protein has an aminoacid sequence as shown in Uniprot Accession number P05231.

In one embodiment, IL-6 is added to the cholangiocyte induction medium of the invention in a concentration ranging from 1 to 50 ng/ml, preferably at about 10 ng/ml. IL-6 can be purchased from Miltenyi.

The population of hepatoblasts (HB) may be cultured for 2 to 15 days, to produce the population of cholangiocytes.

When the population of human hepatoblasts (HB) is a population of human pluripotent stem cells-derived HB, said population of human pluripotent stem cells-derived HB may be cultured for 2 to 10 days, preferably 6 days, to produce the population of cholangiocytes. When the population of human hepatoblasts (HB) is a population of HepaRG-derived HB, said population of HepaRG-derived HB may be cultured for 2 days.

The expression of one or more cholangiocyte markers and/or one or more hepatoblast markers may be monitored and/or detected in the population of differentiating cells.

In one embodiment, when the population of human hepatoblasts (HB) is a population of human pluripotent stem cells-derived HB, the step (ii) comprises the steps of:

(a) culturing the population of hHB in a first cholangiocyte induction medium, wherein said first cholangiocyte induction medium is a CDM comprising growth hormone (GH); and (b) further culturing the population of hHB in the cholangiocyte induction medium which has IL-6 activity.

In a preferred embodiment, when the population of human hepatoblasts (HB) is a population of human pluripotent stem cells-derived HB, the step (ii) comprises the steps of:

(a) culturing the population of hHB in a first cholangiocyte induction medium, wherein said first cholangiocyte induction medium is a CDM comprising both growth hormone (GH) and epidemal growth factor (EGF);

(b) further culturing the population of hHB in the cholangiocyte induction medium which has IL-6 activity; and (c) further culturing the population of hHB in a third cholangiocyte induction medium, wherein said third cholangiocyte induction medium in a CDM comprising sodium taurocholate hydrate and optionally sodium butyrate.

As used herein, the term "Growth hormone" (GH) refers to a peptide hormone that stimulates growth and metabolism. GH has not only a mitogenic but also a developmental effect in liver. It stimulates the synthesis of liver-specific transcription factors. The naturally occurring human GH protein has an aminoacid sequence as shown in Uniprot Accession number P01241.

In one embodiment, GH is added to the culture medium of the invention in a concentration ranging from 1 to 100 ng/ml, preferably at about 50 ng/ml. GH can be purchased from Sigma.

As used herein, the term "Epidemal growth factor" (EGF) refers to a growth factor that stimulates cell growth, proliferation, and differentiation by binding to its receptor EGFR. The naturally occurring human EGF protein has an aminoacid sequence as shown in Uniprot Accession number P01133.

In one embodiment, EGF is added to the culture medium of the invention in a concentration ranging from 1 to 100 ng/ml, preferably at about 25 ng/ml. EGF can be purchased from Peprotech.

As used herein, the term "Sodium taurocholate hydrate" refers to the compound having the following formula:

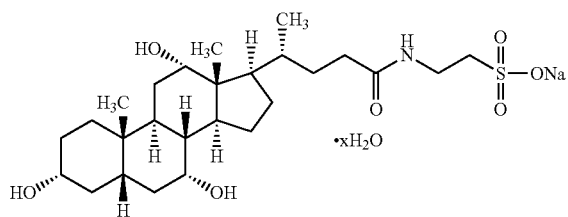

In one embodiment, sodium taurocholate hydrate is added to the culture medium of the invention in a concentration ranging from 1 to 100 μM, preferably at about 10 μM. Sodium taurocholate hydrate can be purchased from Sigma.

In a particular embodiment, the population of hHB is cultured for at least 3 days in each of steps a) to c).

In a preferred embodiment, the step (ii) (b) comprises the steps of:

(x) culturing for 3 days the population of hHB in the cholangiocyte induction medium which has IL-6 activity;

(y) further passaging at least one time the population; and (z) further culturing for another 3 days the population of hHB in the cholangiocyte induction medium which has IL-6 activity.

In a still preferred embodiment, the population of hHB has been passaged at least one time before culturing the population in a cholangiocyte induction medium.

To maintain proliferating cells in culture for an extended period of time, it is necessary to subculture the cells (remove them from one culture vessel, and place them in a new culture vessel containing fresh medium and a lower cell concentration). Each time a population of cells is subcultured, it is referred to as a "passage". In order to move the cells from the first culture vessel to the second culture vessel, the monolayer of cells have to be detached from the surface of the first culture vessel.

Analysis of passaged population can be performed by cell sorting methods. These methods can be used to determine the composition of heterogeneous cell populations, and to isolate specific subpopulations of cells with desirable characteristics which can then be used to conduct further research, or used therapeutically in a clinical setting. Cell sorting methods can only be used effectively on single cells.

When the culture has grown to confluence, human hepatoblasts (hHB) are passaged to another culture vessel. The determination to passage the cells and the techniques for accomplishing such passaging can be performed in accordance with the culture methods of invention (e.g., through morphology assessment and dissection procedures).

Moreover, adhesion between cells or between cells and substrate is needed for growth and division of normal cells, and proteins (extracellular matrix) present between cells or between the cells and the substrate are also needed. In the method of inducing differentiation to choloangiocytes according to the invention, the extracellular matrices described below may be added in the steps above. Examples of the extracellular matrices include matrigel, fibronectin, vitronectin, laminin, nidogen, tenascin, thrombospondin, type-I collagen, type-IV collagen, gelatin, and synthetic substrates equivalent thereto, and in the invention, type-I collagen can be used particularly favorably. Specifically, they can be used, as they are coated on or added to a container for culture.

In one embodiment, the population of hHB is passaged on type-I collagen.

In another embodiment, when the population of human hepatoblasts (HB) is a population of HepaRG-derived HB, the step (ii) comprises the steps of:

(a) culturing the population of hHB in the cholangiocyte induction medium which has IL-6 activity; and (b) further culturing the population of hHB in a second cholangiocyte induction medium, wherein said second cholangiocyte induction medium in a CDM comprising sodium taurocholate hydrate and optionally sodium butyrate.

In a preferred embodiment, when the population of human hepatoblasts (HB) is a population of HepaRG-derived HB, the step (ii) comprises the steps of:

(a) culturing for 2 days the population of hHB in the cholangiocyte induction medium which has IL-6 activity;

(b) further culturing for 2 days the population of hHB in a second cholangiocyte induction medium, wherein said third cholangiocyte induction medium in a CDM comprising sodium taurocholate hydrate and optionally sodium butyrate; and (c) further culturing for 2 days the population of hHB in a third cholangiocyte induction medium, wherein said third cholangiocyte induction medium in a CDM comprising sodium taurocholate hydrate and sodium butyrate.

As previously described, the population of hHB is a population of human pluripotent stem cells-derived HB or HepaRG-derived HB.

HepaRG is a well-characterized human hepatoma cell line which is permanently able to differentiate into mature hepatocytes from a stage of bipotent progenitors[13] and which is widely used for pharmaco-toxicology assays.[14] Such human hepatoma cell line has been described in the international patent application No WO 03/004627 which is hereby incorporated by reference in its entirety.

As used herein, the term "pluripotent" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

More specifically, human pluripotent stem cells may express at least some, and optionally all, of the markers from the following non-limiting list: SSEA-3, SSEA-4, TRA-I-60, TRA-I-81, TRA-2-49/6E, ALP, Sox2, E-cadherin, UTF-I, OCT4, LIN28, REX1, and NANOG.

In a particular embodiment, the human pluripotent stem cells are human embryonic stem cells (hESCs) or human induced pluripotent stem cells (hiPSCs).

As used herein, the term "embryonic stem cells" refers to embryonic cells, which are capable of differentiating into cells of all three embryonic germ layers (i.e., endoderm, ectoderm and mesoderm), or proliferating in an undifferentiated state. Such cells may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

The embryonic stem cells may be obtained using well-known cell-culture methods. For example, human embryonic stem cells can be isolated from human blastocysts. Human blastocysts are typically obtained from human in vivo preimplantation embryos or from in vitro fertilization-derived (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843, 780].

Commercially available stem cells may also be used. Human ES cells can be purchased from the NIH human embryonic stem cells registry (http://escr.nih.gov). Non-limiting examples of commercially available embryonic stem cell lines are BG01, BG02, BG03, BG04, CY12, CY30, CY92, CY10, TE03, TE32, H9 and WA09.

As used herein, the term "induced pluripotent stem cell" refers to a pluripotent stem cell artificially derived from a non-pluripotent cell. A non-pluripotent cell can be a cell of lesser potency to self-renew and differentiate than a pluripotent stem cell. Cells of lesser potency can be, but are not limited to, somatic stem cells, tissue specific progenitor cells, primary or secondary cells. iPSCs have been reproducibly obtained by reprogramming different cell types by forced expression of the OCT4, SOX2, c-MYC and KLF4 transcription factor cocktail or by an alternative combination of factors, substituting KLF4 and c-MYC by NANOG and LIN28. As used herein, the term "reprogramming" refers to the process of changing the fate of a target cell into that of a different cell type, caused by the expression of a small set of factors (or reprogramming factors) in the target cells.

Methods for generating induced pluripotent stem cells based on expression vectors encoding reprogramming factors have been described in the art, see for example WO2007/69666, EP2096169-A1 or WO2010/042490.

Expression vectors for ectopic expression of the reprogramming factors may be, for example, plasmid vector, cosmid vector, bacterial artificial chromosome (BAC) vector, transposon-based vector (such as PiggyBac) or viral vector.

Alternatively, the reprogramming factors, for example, Oct4, Sox2, Klf4 and c-Myc, or corresponding coding DNA or RNA, are introduced into the target cells without integration of exogenous genetic material in the host DNA, i.e. without introduction of the nucleotide sequence in the cell's genome. An expression vector such as a plasmid vector can be delivered into said cells for ectopic expression of the reprogramming factor, in the form of naked DNA. Alternatively, RNAs coding for said reprogramming factors either chemically modified or not, can be introduced into the cells to reprogram them (see for example Warren L, et al, 2010, Cell Stem Cell. November 5; 7(5):618-30). Other expression vectors have been described for example in WO 2009115295.

In one embodiment, the hiPSCs are derived from cells obtained from a healthy subject. In another embodiment, the hiPSCs are derived from cells obtained from an subject with a cholangiopathy and the cholangiocytes in the population display a disease phenotype.

As used herein, the term "cholangiopathy" refers to diseases including primary biliary cirrhosis, primary sclerosing cholangitis, AIDS cholangiopathy, disappearing bile duct syndromes, Alagille's syndrome, cystic fibrosis, and biliary atresia.

In one embodiment, the population of human pluripotent stem cells-derived HB is obtained by a method for inducing hepatic differentiation comprising the steps of:

(i) providing a population of human pluripotent stem cells;

(ii) culturing the population in a endoderm induction medium to produce a population of anterior definitive endoderm (ADE) cells, wherein the endoderm induction medium is a CDM comprising a WNT agonist, a PI3K inhibitor and a TGFβ ligand;

(iii) culturing the population of ADE cells in a hepatic induction medium to produce a population of specified hepatic endodermal cells, wherein the hepatic induction medium is a CDM comprising a fibroblast growth factor (FGF) and a bone morphogenic protein (BMP); and (iv) culturing the population of specified hepatic endodermal cells in a hepatic maturation medium to produce a population of hHB, wherein the hepatic maturation medium is a CDM comprising a FGF, hepatic growth factor (HGF), EGF and retinoic acid (RA).

In a particular embodiment, the population of human pluripotent stem cells-derived HB is obtained by a method for inducing hepatic differentiation comprising the steps of:

(i) providing a population of human pluripotent stem cells;

(ii) culturing the population in a endoderm induction medium to produce a population of anterior definitive endoderm (ADE) cells, wherein the endoderm induction medium is a CDM comprising WNT3a, LY294002 and Activin A;

(iii) culturing the population of ADE cells in a hepatic induction medium to produce a population of specified hepatic endodermal cells, wherein the hepatic induction medium is a CDM comprising FGF2 and BMP4; and (iv) culturing the population of specified hepatic endodermal cells in a hepatic maturation medium to produce a population of hHB, wherein the hepatic maturation medium is a CDM comprising FGF4, HGF, EGF and RA.

As used herein, the term "Anterior Definitive Endoderm" (ADE) refers to cells which typically express endoderm markers, such as SOX17, FOXA2, GSC, MIXL11, LHX1, CXCR4, GATA6, EOMES and HEX. Anterior definitive endoderm (ADE) cells may lack expression of pluripotency markers or markers associated with ectodermal or mesodermal lineages. For example the ADE cells may not express at detectable levels one or more, preferably all, of the following; OCT4, SOX2, alkaline phosphatase, SSEA-3, NANOG, SSEA-4, TRA-1-60 and KLF-4.

At step ii), the endoderm induction medium is a CDM comprising a WNT agonist, a PI3K inhibitor and a TGFβ ligand;

As used herein, the term "WNT agonist" refers to a compound (natural or synthetic) which is effective to activate the WNT signaling.

In a particular embodiment, the WNT agonist is WNT3a as described in Marson et al. 2009 and the international patent application No WO 2009/032194. The naturally occurring human WNT3a protein has an amino acid sequence as shown in Uniprot Accession number P56704.

For example, the endoderm induction medium may contain 10 to 100 ng/ml WNT agonist, such as WNT3a, preferably about 50 ng/ml.

Other WNT agonists are well known form the skilled man in the art. Non-limiting examples of WNT agonists include chemical compounds belonging to the 5-thiophenepyrimidine class as described in Wang et al. 2009 and in the international patent application WO 2010/056907 (for instance the 2-chloro-N-(2-morpholinoethyl)-4-(4-(thiophen-2-yl)pyrimidin-2-ylamino) benzamide, chemical compounds belonging to the aminopyridine class or to the indirubin structural class (for instance the 6-bromoindirubin-3'-oxime ("BIO") as described in Wang et al. 2009.

As used herein, the term "PI3K inhibitor" refers to a compound (natural or synthetic) which is effective to inhibit PI3K activity. In addition, the inhibitors with a specific activity on PI3K may be preferred. Inhibitors of PI3K are, in most cases, compounds that interfere with the binding of ATP in the binding site of PI3K ATP, thus preventing a more or less specific activity of these kinases. In some cases, inhibitors of PI3K are allosteric inhibitors.

Non-limiting examples of PI3K inhibitors include: LY294002 (Cell Signaling #9901); NVP-BEZ235 (BEZ235) (Novartis); GDC-0941 (Genentech/Roche); GDC-0980 (Genentech); PI-103 (Piramed); XL147 (Exilixis/Sanofi-Aventis); XL418 (Exilixis); XL665 (Exelixis); LY29002 (Eli Lilly); ZSTK474 (Zenyaku Kogyo); BGT226 (Novartis); wortmannin; quercetin; tetrodotoxin citrate (Wex Pharmaceuticals); thioperamide maleate; IC87114; PIK93; TGX-115; deguelin; NU 7026; OSUO3012; tandutinib (Millennium Pharmaceuticals); MK-2206 (Merck); OSU-03012; triciribine (M.D. Anderson Cancer Center); PIK75; TGX-221; NU 7441; PI 828; WHI-P 154; AS-604850; AS-041164 (Merck Serono); AS-252424; AS-605240; AS-604850; compound 15e; 17-P-hydroxywortmannin; PP121; WAY-266176; WAY-266175; BKM120 (Novartis); PKI-587 (Pfizer); BYL719 (Novartis); XL765 (Sanofi-Aventis); GSK1059615 or GSK615 (GlaxoSmithKline); IC486068; SF1126 (Semafore Pharmaceuticals); CAL-101 (Gilead Sciences); LME00084; PX-478 (Oncothyreon); PX-866 (Oncothyreon); PX-867 (Oncothyreon), BAY 80-6946 (Bayer), GSK2126458 (GlaxoSmithKline), INK1117 (Intellikine), IPI-145 (Infinity Pharmaceuticals) Palomid 529 (Paloma Pharmaceuticals); ZSTK474 (Zenyaku Kogyo); PWT33597 (Pathway Therapeutics); TG100-115 (TargeGen); CAL263 (Gilead Sciences); SAR245408 (Sanofi-Aventis); SAR245409 (Sanofi-Aventis); GNE-477; CUDC-907; and BMK120 (Novartis).

In one embodiment, the PI3K inhibitor is LY294002 (a morpholine derivative of quercetin) or 2-(4-Morpholinyl)-8-phenyl-4H-1-benzopyran-4-one. LY294002 may be obtained commercially or synthesized as described in U.S. Pat. No. 5,703,075, the content of which is incorporated herein by reference.

In another embodiment, the PI3K inhibitor is a prodrug of LY294002 comprising a reversibly quaternized nitrogen as described in international patent application WO2004/089925. On example of such prodrug is SF1226 (Semafore Pharmaceuticals) which is composed of the PI3K inhibitor LY294002 conjugated to an RGD targeting peptide.

For example, the endoderm induction medium may contain 1 to 100 μM PI3K inhibitor, such as LY294002, preferably about 10 μM.

As used herein, the term "TGFβ ligand" refers to any peptide of the TGFβ superfamily. Members of the TGFβ superfamily possess a characteristic structure and are well-known in the art. The TGFβ ligand may be Activin or TGF3.

In one embodiment, the TGFβ ligand is Activin (also referred herein as Activin A). Activin is well known in the art and is a dimeric polypeptide which exerts a range of cellular effects via stimulation of the Activin/Nodal pathway (Vallier et al., Cell Science 118:4495-4509 (2005)). The naturally occurring human WNT3a protein has an aminoacid sequence as shown in GeneBank Accession number NP 002183. Activin is readily available from commercial sources (e.g. Stemgent Inc. MA USA).

Conveniently, the concentration of Activin in the medium may be from 10 to 1000 ng/ml, preferably about 100 ng/ml.

In a particular embodiment, the population of human pluripotent stem cells is cultured for 3 days in a endoderm induction medium to produce a population of anterior definitive endoderm (ADE) cells.

At step iii), the hepatic induction medium is a CDM comprising a fibroblast growth factor (FGF) and a Bone morphogenic protein (BMP)

As used herein, the term "Family Growth Factor" (FGF) refers to any naturally occurring compound (e.g. a protein) capable of stimulating cellular growth, proliferation and cellular differentiation by binding to one fibroblast growth factor receptor (FGFR). By binding to one FGFR, the compound increases for example the tyrosine phosphorylation of said receptor.

In one embodiment, the FGF is FGF2 (also known as Basic fibroblast growth factor). The naturally occurring human FGF2 protein has an aminoacid sequence as shown in Uniprot Accession number P09038.

Typically, FGF2 is added to the culture medium of the invention in a concentration ranging from 1 to 50 ng/ml, preferably at about 20 ng/ml. FGF2 can be purchased from Peprotech.

As used herein, the term "Bone morphogenetic protein" (BMP) refers to any growth factors binding to one bone morphogenetic protein receptors (BMPR). By binding to one BMPR, the growth factor results in mobilization of members of the SMAD family of proteins.

In one embodiment, the BMP is BMP4 (also known as Bone morphogenetic protein 4). The naturally occurring human BMP4 protein has an aminoacid sequence as shown in Uniprot Accession number P12644.

Typically, BMP4 is added to the culture medium of the invention in a concentration ranging from 1 to 50 ng/ml, preferably at about 10 ng/ml. BMP4 can be purchased from R&D systems.

In a particular embodiment, the population of ADE cells is cultured for 3 days in a hepatic induction medium to produce a population of specified hepatic endodermal cells.

At step iv), the hepatic maturation medium is a CDM comprising a FGF, hepatic growth factor (HGF), EGF and retinoic acid (RA).

In one embodiment, the FGF is FGF4 (also known as heparin secretory transforming protein 1 or Kaposi sarcoma oncogene). The naturally occurring human FGF4 protein has an aminoacid sequence as shown in Uniprot Accession number P08620.

Typically, FGF4 is added to the culture medium of the invention in a concentration ranging from 1 to 50 ng/ml, preferably at about 30 ng/ml. FGF4 can be purchased from Peprotech.

As used herein, the term "Hepatic growth factor" (EGF) refers to a growth factor which regulates cell growth, cell motility, and morphogenesis by activating a tyrosine kinase signaling cascade after binding to the proto-oncogenic c-MET receptor. The naturally occurring human HGF protein has an amino acid sequence as shown in Uniprot Accession number P14210.

In one embodiment, HGF is added to the culture medium of the invention in a concentration ranging from 1 to 100 ng/ml, preferably at about 25 ng/ml. HGF can be purchased from Peprotech.

In one embodiment, EGF is added to the culture medium of the invention in a concentration ranging from 1 to 100 ng/ml, preferably at about 50 ng/ml. EGF can be purchased from Peprotech.

In one embodiment, RA is added to the culture medium of the invention in a concentration ranging from may be from $10^{-8}$M to $10^{-6}$ M, preferably at about $10^{-7}$ M. RA can be purchased from Sigma.

In a particular embodiment, the population of specified hepatic endodermal cells is cultured between 2 and 4 days in a hepatic maturation medium to produce a population of hHB.

In another aspect, the invention relates to a method for obtaining a population of human pluripotent stem cells-derived HB comprising the steps of:

(i) providing a population of human pluripotent stem cells;

(ii) culturing the population in a endoderm induction medium to produce a population of anterior definitive endoderm (ADE) cells, wherein the endoderm induction medium is a CDM comprising a WNT agonist, a PI3K inhibitor and a TGFβ ligand;

(iii) culturing the population of ADE cells in a hepatic induction medium to produce a population of specified hepatic endodermal cells, wherein the hepatic induction medium is a CDM comprising a fibroblast growth factor (FGF) and a bone morphogenic protein (BMP); and (iv) culturing the population of specified hepatic endodermal cells in a hepatic maturation medium to produce a population of hHB, wherein the hepatic maturation medium is a CDM comprising a FGF, HGF, EGF and retinoic acid (RA).

In one embodiment, the population of human pluripotent stem cells-derived HB is obtained by a method for inducing hepatic differentiation comprising the steps of:

(i) providing a population of human pluripotent stem cells;

(ii) culturing the population in a endoderm induction medium to produce a population of anterior definitive endoderm (ADE) cells, wherein the endoderm induction medium is a CDM comprising WNT3a, LY294002 and Activin A;

(iii) culturing the population of ADE cells in a hepatic induction medium to produce a population of specified hepatic endodermal cells, wherein the hepatic induction medium is a CDM comprising FGF2 and BMP4; and (iv) culturing the population of specified hepatic endodermal cells in a hepatic maturation medium to produce a population of hHB, wherein the hepatic maturation medium is a CDM comprising FGF4, HGF, EGF and RA.

Populations of Cholangiocytes According to the Invention and Pharmaceutical Compositions Comprising them In another aspect, the invention also relates to a population of cholangiocytes obtainable by a method as defined above.

In one embodiment, the cholangiocytes display a normal phenotype

In another embodiment, the cholangiocytes display a genetic mutation, in particular genetic mutation that affects key protein within cholangiocytes and which is associated with a cholangiopathy. It should be noted that, the genetic mutation or defect which is responsible for the disease phenotype may be corrected in vitro. Various techniques are available to correct genetic mutations or defects in isolated mammalian cells.

Genetic Modification of Cholangiocytes of the Invention

The term "genetically modified" indicates that the cholangiocytes comprise a nucleic acid molecule not naturally present in non-modified cholangiocytes, or a nucleic acid molecule present in a non-natural state in said cholangiocytes (e.g., amplified). The nucleic acid molecule may have been introduced into said cells or into an ancestor thereof (such as iPS which contains a cholangiopathy associated genetic mutation).

A number of approaches can be used to genetically modify cholangiocytes, such as virus-mediated gene delivery, non-virus-mediated gene delivery, naked DNA, physical treatments, etc. To this end, the nucleic acid is usually incorporated into a vector, such as a recombinant virus, a plasmid, phage, episome, artificial chromosome, etc.

In a particular embodiment of the invention, the cholangiocytes cells are genetically modified using a viral vector (or a recombinant virus). In this embodiment, the heterologous nucleic acid is, for example, introduced into a recombinant virus which is then used to infect cholangiocytes. Different types of recombinant viruses can be used, in particular lentivirus.

In a preferred embodiment, said lentivirus encodes an immortalizing protein, such as SV40T, hTERT, CDK4, etc.

In another preferred embodiment, said lentivirus encodes a wild-type protein (such a protein usually displaying a disease associated genetic mutation in patients suffering from a cholangiopathy) such as wild-type CFTR, PC1 and PC2 proteins. Other genetic mutations involved in cholangiopathies have been previously described[46].

In one embodiment, the nucleic acid sequence encoding the protein of interest (for instance an immortalizing protein or a wild-type protein used for correcting a disease phenotype) is operatively linked to a promoter.

As used herein, the term "operably linked" means that the components described are in a relationship permitting them to function in their intended manner. Thus, a nucleic acid sequence is "operably linked" when placed into a functional relationship with another sequence nucleic acid sequence. For instance, a promoter is "operably linked" to a coding sequence if the promoter causes the transcription of the coding sequence. Generally, operably linked means the linked nucleic acid sequences are contiguous.

As used herein, the term "promoter" refers to a DNA sequence that determines the site of transcription initiation for an RNA polymerase. A promoter may comprise a RNA polymerase III promoter that can provide high levels of constitutive expression across a variety of cell types and will be sufficient to direct the transcription of a distally located sequence, which is a sequence linked to the 3' end of the promoter sequence in a cell. Suitable promoters include, for example, constitutive, regulated, tissue-specific or ubiquitous promoters, which may be of cellular, viral or synthetic origin.

In one embodiment, the promoter is a constitutive promoter such as human elongation factor-1 alpha (EF-1 alpha) etc.

In another embodiment, the promoter is a cholangiocyte-specific promoter such as CK7, TGR5, SCTR, etc.

Importantly, cholangiocytes are the target of disease in a variety of conditions often known as "cholangiopathies" (also referred as "cholestatic liver diseases"). These diseases include primary biliary cirrhosis, primary sclerosing cholangitis, AIDS cholangiopathy, disappearing bile duct syndromes, Alagille's syndrome, cystic fibrosis, ciliopathies and biliary atresia. As a group, cholangiopathies account for approximately 18% of adult liver transplantations and the majority of pediatric liver transplantations.

The invention also provides a pharmaceutical composition comprising the population of cholangiocytes according to the invention. The pharmaceutical composition may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like. This pharmaceutical composition can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration.

As used herein, the term "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Screening Methods of the Invention

In another aspect, the cholangiocytes of the invention obtained from healthy or diseased patients may also be used advantageously for screening applications in the pharmaceutical industry. Such screening tests can be used to search for new drugs with clinical applications or for toxicology tests. The cholangiocytes according to the invention may for instance be useful for generating cellular models of cholangiopathies as described above.

Accordingly, the invention provides a method of screening for a compound useful in the treatment of cholangiopathy comprising the steps of:
(a) contacting a population of cholangiocytes produced by a method of the invention with a test compound, and;
(b) determining the effect of the test compound on said cholangiocytes.

Test Compounds of the Invention:

In one embodiment, the test compound may be selected from the group consisting of peptides, proteins, peptidomimetics, small organic molecules, aptamers or nucleic acids. For example, the test compound according to the invention may be selected from a library of compounds previously synthesised, or a library of compounds for which the structure is determined in a database, or from a library of compounds that have been synthesised de novo.

In a particular embodiment, the test compound may be selected from small organic molecules. As used herein, the term "small organic molecule" refers to a molecule of size comparable to those organic molecules generally used in pharmaceuticals. The term excludes biological macromolecules (e.g.; proteins, nucleic acids, etc.); preferred small organic molecules range in size up to 2000 Da, and most preferably up to about 1000 Da.

Therapeutic Methods and Uses

One major field of application is cell therapy or regenerative medicine. Regenerative medicine can be used to potentially cure any disease that results from malfunctioning, damaged or failing tissue by either regenerating the damaged tissues in vivo by direct in vivo implanting of a composition comprising cholangiocytes of the invention.

Another aspect of the invention thus relates to a population of cholangiocytes of the invention for use in a method of treatment of the human body.

More particularly, an aspect of the invention relates to a population of cholangiocytes of the invention for use in the treatment of a cholangiopathy.

The invention also relates to a method for treating a cholangiopathy comprising the step of administering a pharmaceutically effective amount of a population of cholangiocytes of the invention to a patient in need thereof.

In the context of the invention, the terms "treating" or "treatment", as used herein, refer to a method that is aimed at delaying or preventing the onset of a pathology, at reversing, alleviating, inhibiting, slowing down or stopping the progression, aggravation or deterioration of the symptoms of the pathology, at bringing about ameliorations of the symptoms of the pathology, and/or at curing the pathology.

As used herein, the term "pharmaceutically effective amount" refers to any amount of a population of cholangiocytes according to the invention (or a pharmaceutical composition thereof) that is sufficient to achieve the intended purpose.

Effective dosages and administration regimens can be readily determined by good medical practice based on the nature of the pathology of the subject, and will depend on a number of factors including, but not limited to, the extent of the symptoms of the pathology and extent of damage or degeneration of the tissue or organ of interest, and characteristics of the subject (e.g., age, body weight, gender, general health, and the like).

For therapy, populations of cholangiocytes and pharmaceutical compositions according to the invention may be administered through different routes. The dose and the number of administrations can be optimized by those skilled in the art in a known manner.

In one embodiment, the cholangiocytes of the invention may be useful for autologous regenerative therapy of a patient suffering from cholangiopathy in need of regenerative therapy due to specific disorders or treatments associated to such disorders, including without limitation, Alagille's syndrome and cystic fibrosis due to the deficit in one identified gene that can be replaced in vitro.

In one embodiment, the invention relates to the cholangiocytes of the invention for use as a cell therapy product for implanting into a human patient, as an allogenic graft or, after genetic correction, as an autologous graft (i.e the cells have the same genotype as the patient's cells).

In one embodiment the cholangiocytes of the invention may be useful for bioengineered livers: either by infusing them together with other hepatic cells into a decellularized liver, by generation of vascularized and functional human liver from human iPSCs by transplantation of liver buds created in vitro (Takebe et al Nature 2013 499), by 3D printing or every other method to generate liver tissue.

The invention will be further illustrated by the following figures and examples. However, these examples and figures should not be interpreted in any way as limiting the scope of the present invention.

FIGURES

FIG. 1: Generation of hepatoblasts from human embryonic stem cells (hESCs). (A) Protocol to differentiate hESCs into progenitors. (B) Images showing the sequential morphological changes that occur to give a polygonal shape after 10 days of culture in appropriate conditions.

Figure 2:
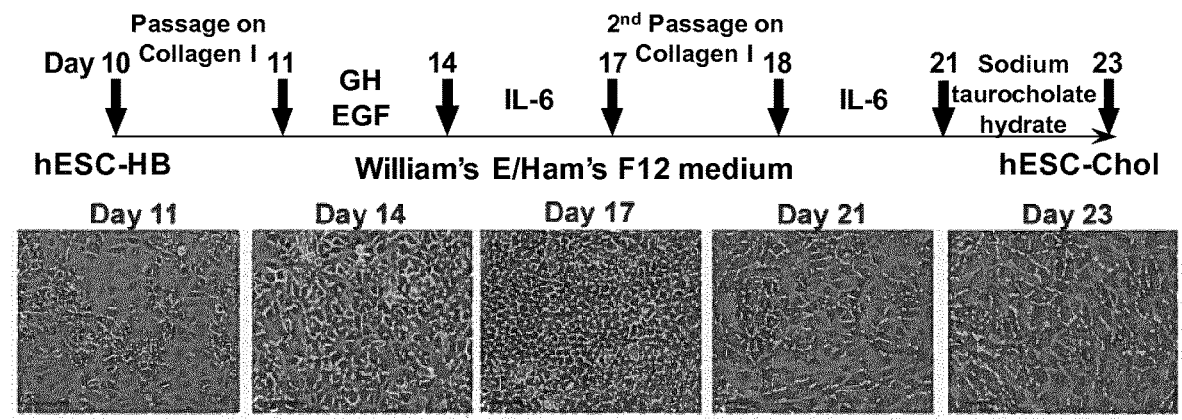

FIG. 2: hESC-derived hepatoblasts differentiate into cholangiocytes. Diagram summarizing our cholangiocytic differentiation protocol. HESC that had been maintained in a feeder-free condition were differentiated into hepatoblasts before passaging onto collagen I-treated wells then induced into cholangiocytic differentiation. Cells were grown 3 days in GH and EGF then IL-6. At day 17, cells reached confluency and were replated onto collagen I-treated wells. Cells were further differentiated for 3 days in IL-6, then for 3 additional days in sodium taurocholate hydrate.

Figure 3:
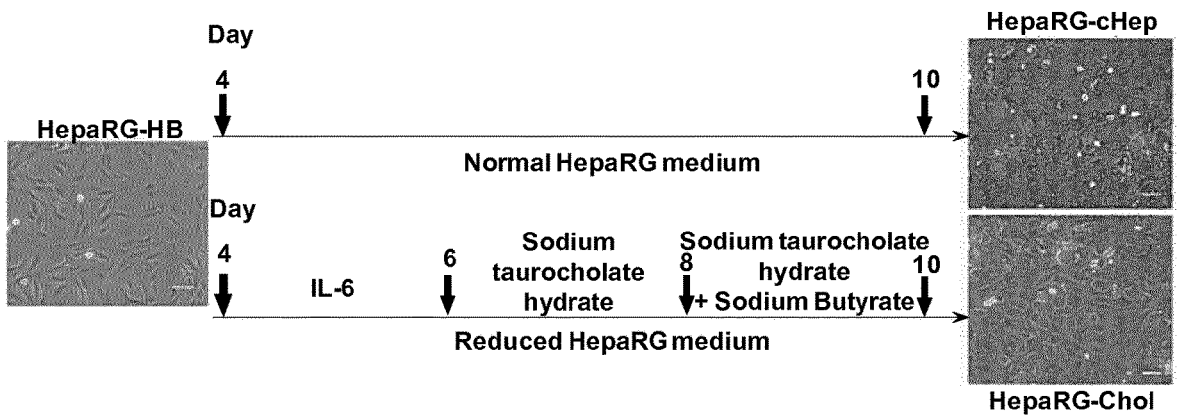

FIG. 3: Differentiation of HepaRG-hepatoblasts into cholangiocytes. Diagram of both protocols for HepaRG cell differentiation from the progenitor stage into hepatocytes or cholangiocytes. Scale bar=50 μm.

EXAMPLE

Material & Methods

Cell Culture:

H9 hESCs (WA09, WiCell, Madison) were maintained on irradiated mouse embryonic fibroblast (MEF) feeder cells (Globalstem), in DMEM/F12 medium supplemented with 20% knockout serum replacement, 1 mM L-glutamine, 1% non-essential amino acids (all from Gibco), 0.1 mM β-mercaptoethanol (Sigma M3148), and 4 ng/ml FGF2 (R&D systems) at 37° C./5% $CO_2$. Cells were passaged once a week with collagenase IV (1 mg/ml Gibco) and plated onto 0.1% gelatin-coated 60 mm culture dishes (Corning) for amplification before starting the differentiation. During this period feeder-free hESCs were maintained as described previously.[11] HiPSC line iPS P2 was already established in the laboratory from human foreskin fibroblasts (CRL 2097, ATCC). IPS P2 cells were maintained on MEF feeders in the same medium, and conditions described for hESCs and were passaged once a week. Prior to differentiation, iPS P2 cells were plated on culture dishes pre-coated with 2 mg/ml Geltrex (Life technologies A1413302). hiPSCs were maintained in Nutristem medium (Stemgent) at 37° C./5% $CO_2$ for a few passages before starting differentiation.

HepaRG cell line was cultured as previously described.[13,14] Four days after seeding, HepaRG displayed hepatic progenitor features (HepaRG-HB). At this step, when maintained in classical HepaRG medium during six days cells are engaged in hepatic lineage (HepaRG-cHep). For complete hepatocyte differentiation (HepaRG-Hep) HepaRG-HB were maintained for two weeks in the classical culture medium, and the culture medium was then supplemented with 2% DMSO for two additional weeks. In this study, to prevent spontaneous differentiation along hepatocytic lineage, and to promote cholangiocyte differentiation HepaRG-HB were cultured in a reduced medium: William's E medium with reduced fetal bovine serum (2%), insulin (1 μg/ml), and hydrocortisone hemisuccinate (1 μM).

hESC/hiPSC Differentiation into Hepatic Progenitor Cells:

One day before passage of hESCs/hiPSCs for differentiation, 12-well plates (Corning, Corning Life Sciences, Dutscher) were coated with 0.1% porcine gelatin (Sigma G1890) for one hour at room temperature, then with coating medium (DMEM, 10% Fetal bovine serum (FBS, Hyclone), 1% non-essential amino acids and 2% L-glutamine), and incubated for 24 h at 37° C. The following day, feeder-free hESCs were plated on the coated plates in CDM-BSA medium supplemented with 10 ng/ml Activin A and 12 ng/ml FGF2. To start differentiation, hESCs/hiPSCs maintenance medium was replaced by RPMI supplemented with B27 serum-free supplement (Life technologies 17504-044) and cells were changed daily thereafter. During the first five days of definitive endoderm differentiation, 100 ng/ml Activin A and $10^{-5}$ M LY294002 (VWR) were added to the medium. Wnt3a (50 ng/ml) (R&D systems) was also added to the hiPSC's medium during the first 3 days of differentiation. To induce the hepatic specification of endoderm, 20 ng/ml FGF2, 10 ng/ml BMP4 (R&D systems) and 50 ng/ml Activin A were added for 3 days. After three days of hepatic specification, the medium was supplemented with 30 ng/ml FGF4 (R&D systems), 25 ng/ml HGF (Peprotech), 50 ng/ml EGF (Peprotech) and $10^{-7}$ M Retinoic acid (Sigma 82625) for two to four days to obtain hepatoblasts.

Differentiation of hESC/hiPSC-Derived Hepatoblasts into Cholangiocytes:

At days 10-12 of differentiation, hESC/hiPSC-hepatoblasts were harvested with cell dissociation buffer (0.1 mg/ml EDTA, 0.5 mg/ml BSA in PBS) and seeded onto 12-well collagen I-coated plates (BD Biosciences) with plating medium (William's E/Ham F12 1:1, 10% FBS (PAA Laboratories), 1 mg/ml fraction V fatty acid-free BSA (Sigma), 1 mM L-glutamine) for 4 hours. Cells were then incubated overnight with biliary differentiation medium (BDM) (William's E/Ham F12 1:1, $10^{-5}$ M linoleic acid-Albumin (Sigma L9530), $5.10^{-8}$ M 3,3',5-Triiodo-L-thyronine (Sigma T2752), 0.2 IU Insulin, $6.10^{-4}$ M Vitamin C (Boyer), $6.10^{-4}$ M human apo-transferrin (Sigma T5391), 1 mM sodium pyruvate (Gibco)). The next day, cells were incubated with BDM supplemented with 50 ng/ml human growth hormone (GH, Sigma H5916) and 25 ng/ml EGF for three days. Cells were then incubated with 10 ng/ml Interleukin-6 (IL-6 Miltenyi 130-093-929) for another three days. At day 17, cells were passaged on collagen I-coated 12-well plates as described for the first passage. At day 18, BDM medium was supplemented with 10 ng/ml IL-6 for three days. Finally, the cells were incubated in 10 μM sodium taurocholate hydrate (Sigma 86339) for 2 days. For the transcriptome analysis, 1 μM Sodium Butyrate (NaBut Sigma 303410) was added to the medium between days 21 to 23 (2 days). Three independent differentiation experiments were performed for hESCs and hiPSCs. Phase-contrast images were taken with a Nikon Eclipse microscope.

Differentiation of HepaRG Progenitors into Cholangiocytes:

HepaRG-HB cultured in the reduced medium were treated for 2 days with IL-6 (10 ng/ml), then for 2 days with sodium taurocholate hydrate (10 nM) and then for 2 days with sodium taurocholate hydrate (10 nM) and sodium butyrate (1.8 μM) to prevent spontaneous differentiation along the hepatocytic lineage. Independent culture experiments were performed 4 times. For proliferation assay, VEGF-165 (20 ng/ml) (Promokine, C-64420) was added on HepaRG-Chol culture for 2 days. Immunostaining pictures were analyzed and quantification was assessed with Cell Health Profiling BioApplication from Cellomics software.

PCR and Quantitative RT-PCR (qRT-PCR):

Total RNA was purified with an RNAeasy kit (Qiagen). cDNAs were obtained by using QuantiTect kit (Qiagen 204341) or the High Capacity cDNA Reverse Transcription Kit (Applied Biosystems, Carlsbad, Calif.) according to the manufacturer's instructions. The level of gene expression was measured and analyzed by real-time PCR over 40 cycles using Taqman universal master mix II and Taqman gene expression assays (Applied Biosystems) using an ABI-7000 real-time PCR system and ABI 7000 software. The expression level of CFTR TGR5 (GPBAR-1), SCTR, GGT1, SOX9, AQP1 and JAG was determined in relation to RPL13A, which served as a housekeeping gene. Simple PCR assays were performed using Platinum Taq DNA polymerase (Invitrogen 10966-034) according to the manufacturer's instructions.

For HepaRG, the Real-time PCR was performed with the fluorescent dye SYBR Green methodology using the SYBR Green PCR Master Mix (Applied Biosystems). Data were quantified with the StepOne Plus software v2.2.1.

Cellular $Ca^{2+}$ Imaging:

At day 17, differentiating hESC-Chols were plated on glass coverslips coated with type I collagen and differentiated further into cholangiocyte-like cells as described above. At day 23 hESC-Chols were loaded with 3 μM Fura2-AM (Invitrogen, F1201) in BDM medium (37° C. and 5% $CO_2$), for 45 minutes. Cells were then washed twice, and transferred into a perfusion chamber placed on the stage of a Zeiss inverted microscope (Axiovert 35). Intracellular calcium increases were measured after stimulation with somatostatin (Eumedica), ATP (Sigma), or Acetylcholine (Sigma). Calcium imaging was performed as described previously.[41] Fluorescence images were collected by a charge-coupled device camera (Princeton), digitized and integrated in real time by an image processor (Metafluor, Princeton).

3D Cell Culture Assays for Cyst Formation:

hESC/hiPSC- or HepaRG-chol were detached with trypsin and dissociated to reach a single cell suspension. Cells were then suspended in a mixture of rat-tail type I collagen (BD Biosciences), Matrigel 40% (BD Biosciences), HEPES (0.02M) and $NaHCO_3$ (2.35 mg/ml). A cell suspension containing 5000 cells was added to 24-well inserts (BD biosciences 353104) and incubated at 37° C. for 3 hours. For hESC-, hiPSC-Chol, one ml of BDM medium supplemented with 20 ng/ml HGF and 10 ng/ml EGF, and for HepaRG-Chol one ml of reduced HepaRG medium, supplemented with 20 ng/ml HGF and 10 ng/ml EGF was added on top of the insert as well as in the well, and incubated at 37° C./5% $CO_2$ up to 2 weeks.

Immunocytochemistry:

Cells were fixed with 4% Paraformaldehyde for 15 minutes at room temperature and permeabilized with 0.5% Triton X-100 for 15 minutes, 3% BSA-PBS for 30 minutes at room temperature or with 0.2% saponin and 5% donkey serum for 45 minutes at room temperature. Primary antibodies were diluted in 1% BSA-PBS, and incubated overnight at 4° C. Secondary antibodies were diluted in 1% BSA-PBS and incubated for 1 hour at room temperature. Cell nuclei were stained with DAPI or Hoechst H33342 (Sigma B2261) and cells were mounted in Fluoromount medium (Sigma F4680). CO-029 antibody (mouse, 1/100 dilution) was a kind gift from Dr Claude Boucheix (UMR-S 1004, Villejuif). (See primary and secondary antibodies' dilutions in Supporting Table 5). All the photographs were taken with a Leica HMR microscope (Leica Microsystems), inverted DMIRBE microscope (Leica) using a 20x/0.4 N Plan objective (leica) and a CoolSnapES N&B camera (Photometrics) driven by MetaVue software (Molecular devices), SP5 LEICA DMI 6000 CS Microscope (Leica, Germany) and treated with LAS AF 2.6.0 software, or ACT-1 Nikon software or Cellomics ArrayScan VTI HCS Reader.

3D cell culture immunostaining was performed as described[42]. Briefly, cysts were fixed with 3% paraformaldehyde for 20 min, permeabilized with 0.5% PBS-Triton X-100 for 10 min, and quenched for 15 min with a glycine/PBS solution (130 mM NaCl, 7 mM $Na_2HPO_4$, 3.5 mM $NaH_2PO_4$, and 100 mM glycine). Cells were incubated in primary block (10% FBS, 130 mM NaCl, 7 mM $Na_2HPO_4$, 3.5 mM $NaH_2PO_4$, 7.7 mM $NaN_3$, 0.1% BSA, 0.2% PBS-Triton X-100, and 0.05% Tween-20) for 4 hours at room temperature. After washes, cells were incubated overnight in primary block with primary antibodies and DAPI. After washes, cells were incubated for 1 h with secondary antibodies, washed and mounted with Fluoromount medium. 3D culture images of hESCs were taken with a Zeiss LSM510-Meta/Axiovert 200M laser scanning confocal microscope (Carl Zeiss, Iena, Germany) with an Achroplan 40x, NA:0.75 objective lens and scan zoom between 3.5 and 4).

LSM ver4.2 software was used for acquisitions. Confocal images of hiPSCs and HepaRG 3D cultures were taken with an SP5 LEICA DMI 6000 CS Microscope (Leica, Germany). LAS AF 2.6.0 software was used for acquisitions.

Transport of Fluorescent Dye and Fluorescent Bile Salt:

Cysts were incubated in Leibovitz's no phenol red L-15 medium (Gibco) containing 5 µM cholyl-lysyl-fluorescein (CLF, BD-451041) for 15 minutes at 37° C. and 5% $CO_2$. Cells were then washed twice with L-15 medium and fluorescent bile salt internalization was visualized with a SP5 LEICA DMI 6000 CS Microscope (Leica, Germany) equipped with an incubator to maintain the cells at 37° C. during observation.

For rhodamine 123 transport test, cells were incubated in fresh serum-free medium containing 100 µM rhodamine 123 (Sigma R8004) for 5 min and washed with serum-free medium three times. Cysts were incubated with 10 µM verapamil (Sigma), for 30 minutes before adding rhodamine 123. Fluorescence internalization was visualized with a confocal microscope and images were taken after 30 minutes.

Flow Cytometry:

Cells were dissociated with cell dissociation buffer, and suspended in 3% BSA-PBS. They were then incubated with TRA-1-81-PE, SSEA4-PE and CD184-APC, EpCAM-FITC conjugated antibodies or in control isotypes for 30 minutes at 4° C. in the dark. Cells were then washed with PBS, centrifuged and suspended in PBS-BSA 1% for analysis. Cells were detected in FL2 and FL4 channels with an Accuri C6 flow cytometer (BD biosciences). Dead cells were eliminated with 7AAD staining (Beckman coulter A07704). For CFTR analysis, cells were fixed with 4% paraformaldehyde (10 min) and permeabilized with 0.1% PBS-Tween for 20 min. Non-specific sites of interaction were blocked with 3% PBS-BSA. Cells were incubated with anti-CFTR (CF-3) antibody (Abcam) for 30 min at 4° C. and then with the secondary antibody Alexafluor 488 donkey anti-mouse (Molecular probes) for 30 min at room temperature. Cells were then washed twice, suspended in 0.1% PBS-Tween and analyzed in FL1 channel with an Accuri C6 flow cytometer.

Cell Cycle Analysis:

After 3 days of GH/EGF treatment, cells were detached with trypsin, centrifuged and suspended in 3 ml of 70% ethanol and kept at −20° C. On the day of analysis, cells were centrifuged and suspended in 50 µg/ml propidium iodide (Sigma P-4170) and 0.5 mg/ml RNase A (Sigma R6513), kept in the dark at 4° C. for 30 minutes and analyzed with an Accuri flow cytometer.

Western Blot Analysis:

Total proteins were extracted with RIPA buffer. Briefly, 50 µg of total protein was electrophoresed on an 8% acrylamide-SDS gel and then transferred to a PVDF membrane (GE healthcare RPN303F). The membrane was blocked with PBS containing 5% (w/v) dry milk and 0.1% Tween-20, washed with PBS containing 0.1% Tween-20 (PBST) and then incubated with primary antibodies at 4° C. overnight. After washing in PBST, the membranes were incubated with horseradish peroxidase-conjugated secondary antibodies at 37° C. for 1 h. Beta-actin or HSC-70 was used as a control for protein amount.

Microarray analysis: mRNAs from biological replicates of H9 cells, hESC-HB, hESC-Chol, HepaRG-HB, HepaRG-Chol, HepaRG-cHep and HepaRG-Hep were used. The purity and integrity of RNA were evaluated on Agilent Bioanalyser (Agilent Technologies, Palo Alto, Calif., USA). Genome-wide expression profiling was performed using the low-input QuickAmp labeling kit and human SurePrint G3 8×60K pangenomic microarrays (Agilent Technologies, Santa Clara, Calif., USA). Gene expression data were processed using Feature Extraction and GeneSpring software (Agilent Technologies). The data discussed in this publication have been deposited in NCBI's Gene Expression Omnibus and are accessible through GEO Series accession number GSE51791 (http://www.ncbi.nlm.nih.gov/geo/query/acc.cgi?acc=GSE51791). To determine genes significantly deregulated between hESC-HB and hESC-Chol or HepaRG-HB and HepaRG-Chol, a t-test (Bonferroni FWER correction) with a p-value <0.05 and a Fold Change (FC) >2 was used.

Microarray Meta-Analysis:

Home project Agilent chip microarray data were combined with data from different GEO series matrix (GEO data set) publicly available on the website. Public data used are as follows: three samples of the cell line H69 untreated in the set GSE23991 (Illumina humanRef-8 v2.0 annotated with platform GPL6104),[29] and six samples of human normal biliary epithelial cells in the set GSE32225 (WG-DASL Illumina humanRef-8 v3.0 annotated with platform GPL8432).[30] Individual raw data from each GEO dataset and the house experimental set were individually normalized on the standard deviation of the chip. Each GEO experimental set was annotated with their respective GPL platform.

The cross experimental matrix was formed by SQL query. The cross experimental mathematical adjustment was done with the "batchadjust" function in the PAMR package[43] of R software available on the Bioconductor website.[44] The effect of mathematical adjustment was verified by factorial projection by principal component analysis before and after PAMR correction.[45]

Data Clustering:

Global differentially expressed genes during differentiation were identified by a one-way ANOVA test (Bonferroni FWER correction) with a p-value<0.001 and an absolute FC>3. We used Gene Cluster 3.0 software (Euclidean metrics with complete distances) to cluster the set of genes selected by ANOVA and TreeView 1.6 to visualize the clustering. The accuracy of our genomic integration analysis was validated by another analysis with the same number of genes (2920) randomly selected. Heat maps of some gene expression were created by importing data into the Java Treeview. When a gene was represented by more than one probe-set on the array, a single probe-set was chosen to represent gene expression in the heat map according to the highest mean expression over all samples.

Ingenuity Pathway Analysis:

Upstream regulators were identified using upstream regulator analyses in the Ingenuity Pathway Analysis Tool (IPA, Ingenuity Systems, Redwood City, Calif.) based on the down-regulated or up-regulated gene lists. IPA analysis was performed on the 126 up- and 71 down-regulated genes (p<0.05; FC>2) for HepaRG differentiation. IPA was performed on the 489 up- and 307 down-regulated genes (p>0.001; FC>7) for hESC differentiation.

Transduction of Cholangiocyte Progenitors:

Cholangiocyte progenitors were transduced once at day 14 at MOI 30 with a lentivector bearing a EF1α-GFP cassette and were analyzed 4 days later by flow cytometry.

Results

Differentiation of hESCs into Hepatoblasts:

The present strategy to induce differentiation of hESCs into hepatoblasts was based on a previously published protocol[11,12] with some modifications (see Supporting Materials for details). The differentiation protocol is illustrated in FIG. 1A. At day 0, hESCs displayed typical colony morphology of stem cells (FIG. 1B, panel i). The cells expressed pluripotency markers including OCT4, NANOG, TRA-1-60 and SSEA4 and were negative for GATA4, confirming the absence of endodermal differentiation. Flow cytometry analysis showed that more than 70% of the cells expressed TRA-1-81. Five days of endoderm induction treatment resulted in a homogeneous monolayer of polygonal endodermal cells (FIG. 1B, panel ii). Immunostaining revealed that most of the cells were positive for the definitive endoderm markers GATA4, CXCR4, Hepatocyte nuclear factor 3β (HNF3(3) and SOX17. Flow cytometry analysis confirmed that more than 90% of the cells expressed CXCR4. Following the endodermal induction, cells were treated with the hepatic commitment factors for 3 days, which gave rise to specified hepatic endoderm/liver bud (FIG. 1B, panel iii). Immunostaining of these cells confirmed that they expressed characteristic markers HNF3β, HNF4α Cytokeratin 19 (CK19), CK18, SOX9, SOX17, GATA4 and Neural cell adhesion molecule (NCAM). In addition, these cells were negative for α-fetoprotein (AFP) and CK7, the Cytokeratin specifically expressed by cholangiocytes. Most of them (93%) were also positive for Epithelial cell adhesion molecule (EpCAM) as assessed by flow cytometry analysis. Finally, the medium was supplemented with factors inducing differentiation of hepatic endodermal cells into hepatoblasts with a polygonal morphology (FIG. 1B, panel iv). Immunostaining of cells at day 10 showed that they were positive for AFP and CK19. HESC-derived hepatoblasts (hESC-HB) also expressed the transcription factors HNF3β, GATA4, HNF6 and HNF4α. Flow cytometry analysis revealed that most of the cells (87%) remained positive for EpCAM hESC-Derived Hepatoblasts Exhibit the Potential for Commitment Toward Cholangiocyte Precursors:

As NOTCH2 and SALL4, Forkhead factor M1B (FOXM1B) is also reported to be critical for differentiation of precursors toward biliary epithelial cells.[15] To further define the biliary commitment potential of our hepatoblasts, the inventors analyzed the expression of different biliary markers. They found that hESC-HBs expressed FOXM1B, NOTCH2 and SALL4.

The inventors then tested factors known to stimulate cholangiocyte proliferation and differentiation in the prenatal period: Epidermal growth factor (EGF), Growth hormone (GH), a regulator of the insulin-like growth factor-1 pathway,[16] and Interleukin 6 (IL-6)[17] in diverse combinations. GH, a regulator of the insulin-like growth factor-1 pathway, has not only a mitogenic but also a developmental effect in liver. It stimulates the synthesis of liver-specific transcription factors among which HNF6, which enhances SOX9 expression.[18] Both GH and Sox9 negatively regulate CEBP/α which governs transcription of mature hepatocyte marker genes.[19] Finally, IL-6 inhibits GH-mediated gene expression in hepatocytes.[20]

They then tested the effect of sodium taurocholate hydrate, which not only stimulates proliferation and differentiation of cholangiocytes but also displays anti-apoptotic activity on these cells in rat.[21] The present final differentiation strategy is illustrated in FIG. 2.

At the hepatoblast stage (Day 10), cells were passaged on collagen I-coated plates and maintained for one day in William's E/Ham's F12 medium as described in Materials and Methods. Cell cycle analysis showed that after 3 days of GH/EGF the cells were actively proliferating. The percentage of cells in S and G2/M phase was 36% and 8% respectively. Differentiating cells remained in proliferation after addition of IL-6 yielding up to 68% Ki67-positive cycling cells This was confirmed by expression of Cyclin A, Cyclin E, CDK1 and CDK2.

Gene expression of differentiating cells was analyzed after addition of GH/EGF and IL-6 by qRT-PCR. Combination of these factors increased the expression of cholangiocyte markers such as CFTR, G protein-coupled bile acid receptor 1 (TGR5), SOX9 and secretin receptor (SCTR).

In addition, one single transduction of cholangiocyte progenitors yielded to GFP expression in 30% of the cell, suggesting that, according to our experience, a second transduction a few hours after the first one would result in 50-60% of GFP positive cells.

hESC-Derived Hepatoblasts Differentiate into Functional Cholangiocyte-Like Cells:

Treatment of hepatoblasts with GH/EGF then IL-6 allowed the cells to reach confluency around day 17. This population of proliferating biliary-committed cells was then passaged on collagen I. The cells were treated with IL-6 for 3 days and then with sodium taurocholate hydrate for 2 days. In the course of differentiation the cell population progressively acquired a cuboidal morphology (FIG. 2). QRT-PCR analysis revealed a significant increase in gene expression level of cholangiocyte markers such as CFTR, TGR5, Aquaporin-1 (AQP1), SOX9, SCTR and JAG1 in hESC-derived cholangiocytes (hESC-Chol) compared to hESC-HB. The expression level of γ-glutamyltransferase 1 (GGT1) was equivalent to that of hESC-HB and control cells.

In addition, RT-PCR analysis on hESC-Chol revealed that these cells expressed CK7, and also biliary markers including $Cl^-/HCO_3^-$ Anion Exchanger 2 (AE2) and NCAM, a marker of proliferating cholangiocytes.[22] The inventors observed that SALL4, NOTCH2 and FOXM1B, were also expressed in hESC-Chol whereas the stemness marker NANOG was extinguished.

The inventors also evaluated hepatocytic marker expression by qRT-PCR in hESC-Chol. AFP and Albumin (ALB) expression level was $10^4$ and $10^7$ less than in fetal and adult hepatocytes respectively. Aldolase B transcripts were not detectable.

Cholangiocyte differentiation was confirmed by immunostaining analysis, showing that hESC-derived cholangiocytes expressed CK7, CK19, CK18, Osteopontin (OPN), a downstream target of SOX9 during normal development,[23] SOX9, HNF6 and HNF1β, whereas HNF4α expression was not detected, as shown by co-staining experiments with CK7/HNF4α).

In addition, to further confirming the identity of these cholangiocyte-like cells, they tested whether these cells expressed specific biliary receptors. Immunostaining analysis revealed that these cells expressed CFTR, SCTR, Apical $Na^+$-dependent bile acid transporter (ASBT), TGR5 and KDR (VEGFR-2). FACS analysis revealed that 90% of the cells expressed CFTR. They also examined expression of cholangiocyte transporters by Western blot analysis, which confirmed expression of ASBT and TGR5 in hESC-derived cholangiocytes.

By contrast to hepatocytes, cholangiocytes bear primary cilia, which play an important role in modulating the secretory and proliferative functions of fully differentiated cells.[24] The presence of cilia (one cilium per cell) was detected using an antibody to a ciliary marker, acetylated α-tubulin.

To assess the functionality of our hESC-Chol, they analyzed their response to Adenosine triphosphate (ATP), acetylcholine and Somatostatin, known to induce $Ca^{2+}$ increase in biliary cells via P2Y1 receptors,[5] M3 muscarinic receptor (AChR M3),[25] Somatostatin receptor type 2 (SSTR2)[26] respectively, as well as type III Inositol 1,4,5-triphosphate (InsP3) receptor (InsP3R), an intracellular $Ca^{2+}$ channel, which stimulates release of $Ca^{2+}$ from intracellular stores into the cytosol.[27]

RT-PCR on hESC-Chol revealed that the four different receptors were specifically expressed in these cells compared to human hepatocytes. ATP, acetylcholine or Somatostatin stimulation resulted in $Ca^{2+}$ increase. The percentage of responsive cells was quantified to be 70%±5, 40%±4, and 31%±9, respectively.

HepaRG-Progenitor Cells can be Driven to Differentiate into Cholangiocytes:

The inventors then assessed whether the present protocol could be used to drive differentiation of HepaRG to a cholangiocyte lineage. In the present conditions, addition of GH did not improve proliferation and differentiation of HepaRG-hepatoblasts (HepaRG-HB) (data not shown) since they expressed HNF3β and very low level of C/EBPα.[13,14] However, two days of IL-6 followed by 2 days of sodium taurocholate hydrate treatment was sufficient to drive commitment toward cholangiocyte differentiation (FIG. 3). Then, to prevent spontaneous differentiation of HepaRG-HB into hepatocytes, Na Butyrate (NaBut) was added after 2 days of sodium taurocholate hydrate treatment.[28]

At the end of the differentiation protocol (day 10), HepaRG-derived cholangiocytes (HepaRG-Chol) expressed high levels of GGT1, CK19, JAGGED1 and TGR5 compared to hepatocyte-committed HepaRG cells (HepaRG-cHep) and HepaRG-HB.

Immunostaining revealed that HepaRG-Chol cells expressed OPN, CK19, SCTR and Tetraspanin-8 (C0-029), whereas they were not expressed in our regular HepaRG culture conditions. Hepatocytic markers such as ALB and HNF4α were repressed.

Immunostaining of acetylated α-tubulin revealed the presence of primary cilia in HepaRG-Chol. In addition, HepaRG-Chol expressed the receptors P2RY1, AChR M3, SSTR2 and InsP3R at levels similar to that of hESC-Chol.

Finally, since cholangiocytes proliferate in response to VEGF (Vascular endothelial growth factor), we stimulated HepaRG-Chol with VEGF, which induced a significant two-fold increase in the number of cells in G2/M phases.

Transcriptomic Profiles of Cholangiocytes Derived from Both hESCs and HepaRG:

To analyze gene expression profiling in cholangiocytes derived from both hESCs and HepaRG in similar conditions, the inventors first verified that addition of NaBut on hESC-Chol did not significantly change expression of cholangiocyte markers. Microarrays were conducted at day 23 and day 10 of differentiation for hESC-Chol, and HepaRG-Chol respectively and compared to hESC-HB and HepaRG-HB. Integrative genomics was first used to determine the level of differentiation of the cells. The 2920 genes differentially expressed in cholangiocytes (ANOVA) were integrated with gene expression profiles of normal human biliary epithelial cells[29] and of an immortalized human intrahepatic biliary epithelial cell line (H69)[30]. Hierarchical clustering analysis revealed two main branches dividing the samples with regard to the lineage: hESC/hepatoblasts/cholangiocytes in one branch and hepatocytes in the other. Cluster one includes both hESC-Chol and HepaRG-Chol as well as H69 and normal human biliary epithelial cells. Cluster two included HepaRG-Hep and HepaRG-cHep. Cluster one was divided into two branches driven by hESC- or HepaRG-Chol differentiation. HepaRG-Chol clustered with both H69 cell line and human normal biliary epithelial cells. This subdivision probably reflects the origin of the cells. HepaRG cells derive from differentiated hepatocellular carcinoma, normal human biliary epithelial cells were microdissected from six metastatic liver tumors,[30] and H69 cells are SV40-transformed cells.[29]

During hESC-HB differentiation, they found that up to 3429 genes were deregulated (p<0.05; FC>2). In HepaRG-Chol only 197 genes were significantly deregulated (p<0.05; FC>2). Interestingly Ingenuity Pathway Analysis (IPA) revealed that the 489 strongest up-regulated genes (p<0.001; FC>7) in hESC-Chol and the 126 up-regulated genes in HepaRG-Chol were involved in common pathways including Farnesoid X receptor (FXR)/RXR activation pathway. In addition, Vitamin D receptor/Retinoid X receptor (VDR/RXR) was strongly upregulated in hESC-Chol. Two of the main upstream regulators of up-regulated genes were Transforming growth factor beta 1 (TGFβ1) and Estrogen receptor 1 (ESR1), known to play a role in modulating rat cholangiocyte proliferation.[31]

Comparison of both expression profiles of hESC-Chol and HepaRG-Chol highlighted up-regulation of common and distinct genes. For instance, OPN, E-cadherin (CDH1), and KCNN4, a Potassium intermediate-conductance $Ca^{2+}$-activated $K^+$ channel were upregulated in both cell types. By contrast, Peroxysome proliferator activated receptor gamma (PPARγ) or the ABCB8 transporter were specifically upregulated only in hESC-Chol. Other transporters such as ABCA3 and ABCB4 were induced specifically in HepaRG-Chol. Expression of these genes was confirmed by qRT-PCR.

Generation of Cholangiocytes from hiPSCs:

Finally, the inventors investigated whether the culture conditions developed to differentiate hESCs into cholangiocytes could also efficiently drive differentiation of hiPSCs. To this end, they used iPS P2 cell line which was reprogrammed using a polycistronic retroviral vector encoding OCT4, SOX2, KLF4 and C-Myc.[32] iPSCs were characterized for pluripotency markers such as OCT4, NANOG, TRA-1-60 and SSEA4 by immunostaining and flow cytometry. IPS P2 cells were differentiated into hepatoblasts as described for hESCs. Immunostaining confirmed that hiPSC-derived hepatoblasts (hiPSC-HB) expressed hepatic progenitor markers AFP, HNF4α, CK19, HNF6 and HNF3β, whereas they were negative for biliary marker CK7. hiPSC-HB were then differentiated into cholangiocytes (hiPSC-Chol). Analysis of biliary markers expressed in hiPSC-Chol by qRT-PCR revealed a significant increase in CFTR, TGR5 and AQP1 expression compared to that of hiPSC-HB. In addition, hiPSC-Chol expressed biliary markers CK7, CK19, HNF6, SOX9 and CFTR, whereas expression of HNF4α was not detected.

As in hESC-Chol, AFP, ALB and Aldolase B expression level was $10^4$, $10^6$ and $10^6$ less than in fetal and adult hepatocytes respectively. Expression of cholangiocyte-specific calcium signaling receptors SSTR2, P2RY1, InsP3R type III and AChR M3 was confirmed in hiPSC-Chol. Finally, the presence of primary cilia was visualized by immunostaining Taken together, these data suggest that the present approach, developed initially for hESCs, can be used to generate cholangiocyte-like cells from hiPSCs as well as from HepaRG cells.

Functionality of Cholangiocyte-Like Cells Generated from Pluripotent Stem Cells and HepaRG:

To assess the potential of cholangiocytes derived from hESC/hiPSC and HepaRG to form cysts and tubules, the inventors used a three-dimensional culture system. After 7 days of culture, cholangiocytes formed round cysts with luminal space. Moreover, when the cysts were kept in culture for one more week, they were able to bud, and formed branching tubular structures. Of note, HepaRG-cHep cultured in 3D did not form cysts and tubules. Cyst polarity was verified by basolateral and apical localization of β-catenin and F-actin, respectively. A physiological function of cholangiocytes is the secretion of small substances by various transmembrane channel proteins such as multidrug resistance protein 1 (MDR1). After incubation with rhodamine 123, MDR1 substrate, fluorescence accumulation was detected inside the central lumen of hESC/hiPSC/HepaRG-cysts. Furthermore, when cysts were incubated in verapamil, an MDR1 inhibitor, rhodamine 123 transport was abolished. Since MDR1 is also expressed by progenitor cells[33] we further investigated the transport of fluorescent bile salt, a property of functional cholangiocytes. When cysts were incubated with cholyl-lysyl-fluorescein (CLF), fluorescence accumulation was detected inside the central lumen.

DISCUSSION

This present study provides the first evidence of the differentiation of functional cholangiocyte-like cells from hepatic progenitors generated from human pluripotent stem cells and HepaRG cells. The present approach is based on fully defined culture conditions devoid of serum and of feeder cells.

In vivo maturation of hepatoblasts to cholangiocytes is regulated by several factors secreted in the microenvironment around the portal vein, which consists of mesenchymal cells, other cells and extracellular matrix. After liver specification, HNF3β, HNF6 and HNF1β are required for normal bile duct development.[34] HNF1β is a direct target of HNF6 and is also required for duct morphogenesis. The inventors found that these transcription factors were expressed in hepatoblasts and in differentiating cholangiocytes.

As hepatoblasts forming primitive ductal structures respond to periportal mesenchymal cues such as Bone morphogenetic protein 4 (BMP4), TGFβ1 and VEGF, they first analyzed the effect of these factors on hepatic progenitors. They found that addition of these factors did not induce significant cell commitment toward cholangiocytes in our conditions (data not shown).

Therefore, since it seemed difficult to find a signal pathway truly specific for cholangiocytes, they reasoned that addition of GH on hepatoblasts, followed by IL-6 should efficiently trigger these cells toward the cholangiocyte lineage via HNF6 and HNF3β which are restricted to biliary lineage throughout development and are expressed in their hepatoblasts. Interestingly, transcriptome analysis revealed that factors important for ductal plate commitment and/or their downstream targets were activated in both hESC/HepaRG-cholangiocytes. For instance, downstream target genes of TGFβ, including those coding for matrix proteins such as Fibronectin 1, Integrin α6 and Laminin 3, were expressed by both hESC/HepaRG-Chol. Of note, they confirmed by immunostaining that the cells also expressed OPN and VEGFR-2. NOTCH2 and downstream effectors of Transcription factor HES1, a target of NOTCH signaling, were also up-regulated. Altogether, these data suggest that the present differentiation protocol allows activation of appropriate signaling pathways known to be involved in biliary differentiation.

Gene expression profile analysis allowed the inventors to identify a panel of genes and pathways characteristic of cholangiocytes. It is known that cholangiocytes express a subset of nuclear receptors including VDR, FXR, PPAR delta/gamma, ESR1 and ABCA.[35,36] The present data show that most of them were induced in hESC-Chol and most of their downstream targets were activated in both hESC/HepaRG-Chol. Human cholangiocytes also express a variety of Toll-Like-Receptors (TLRs) which mediate (via TLR2 and 4) host epithelial defense responses to microbial infection.[37] Interestingly, TLR4 was significantly induced in hESC-Chol.

Genomic integration of their dataset with gene expression profiles of normal human biliary epithelial cells and H69 cell line confirmed the commitment of progenitors into cholangiocytes. Importantly, both hESC/HepaRG-Chol as well as H69 and normal human biliary epithelial cells clustered in the same branch.

Morphogenesis of the biliary tree is tightly linked to the differentiation of the cholangiocytes that line the lumen of the biliary tree. According to the position of the cholangiocytes along the intrahepatic biliary tree, their size, morphology, proliferation activity and function differ.[38] Small cholangiocytes are thought to be committed biliary progenitors lining the interlobular bile ducts, ductules, and the canal of Hering expressing CK7, CK19, NCAM, CFTR and AQP1, while large cholangiocytes line large ducts and express SCTR, GGT1, TGR5 and AE2.[39] Cholangiocytes also express ASBT, providing a mechanism to mediate bile acid uptake[21] and TGR5 that may function as a bile sensor coupling biliary bile acid concentration to ductular bile formation and bile flow.[40] hESC/hiPSC-Chol and HepaRG-Chol expressed various levels of these markers, suggesting a mixed population containing both types of cholangiocytes. Of note CFTR, ASBT and EpCAM are mutated in HepaRG (Dubois-Pot-Schneider, personal communication).

The present data show that differentiated cholangiocytes express SSTR2, P2RY1, AChR M3 and InsP3R type III receptors, known to be restricted to bile ducts in human liver,[5,25-27] and that their stimulation resulted in an increase of intracellular $Ca^{2+}$. Interestingly, hESC-, HepaRG- and hiPSC-Chol have primary cilia, the sensory organelle present on cholangiocyte apical surface, and form polarized cysts able to transport a fluorescent bile acid. Altogether the present data reveal the functionality of the cholangiocyte-like cells thus obtained and highlight the importance of the in vitro model.

Pathogenic aspects of the most important primary cholangiopathies (polycystic and fibropolycystic liver diseases, Alagille syndrome) are related to altered biliary development, which in some cases (polycystic disease notably), can be due to defects in cilia. Thus cholangiocytes generated by the present approach represent a useful model for studying not only the molecular mechanisms of bile duct development but also the pathogenic mechanisms leading to liver fibrosis or ciliopathies. It may contribute to the development of therapeutic strategies, including those with bioengineered livers.

REFERENCES

Throughout this application, various references describe the state of the art to which this invention pertains. The disclosures of these references are hereby incorporated by reference into the present disclosure.
1. Antoniou A, Raynaud P, Cordi S, Zong Y, Tronche F, Stanger B Z, et al. Intrahepatic Bile Ducts Develop According to a New Mode of Tubulogenesis Regulated by the Transcription Factor SOX9. Gastroenterology 2009; 136:2325-33.

2. Schmelzer E, Wauthier E, Reid LM. The phenotypes of pluripotent human hepatic progenitors. Stem Cells 2006; 24:1852-8.
3. Zhang L, Theise N, Chua M, Reid LM. The stem cell niche of human livers: symmetry between development and regeneration. Hepatology 2008; 48:1598-607.
4. Turner R, Lozoya O, Wang Y, Cardinale V, Gaudio E, Alpini G, et al. Human hepatic stem cell and maturational liver lineage biology. Hepatology 2011; 53:1035-45.
5. Leite M F, Nathanson M H. Signaling Pathways in Biliary Epithelial Cells. In: Dufour J-F, Clavien P-A, Trautwein C, Graf R, editors. Signaling Pathways in Liver Diseases. Springer Berlin Heidelberg; 2005. page 17-26.
6. Strazzabosco M, Fabris L, Spill C. Pathophysiology of cholangiopathies. J Clin Gastroenterol 2005; 39:S90-S102.
7. Humphreys E H, Williams K T, Adams D H, Afford S C. Primary and malignant cholangiocytes undergo CD40 mediated Fas dependent apoptosis, but are insensitive to direct activation with exogenous Fas ligand. PloS One 2010; 5:e14037.
8. Vroman B, LaRusso N F. Development and characterization of polarized primary cultures of rat intrahepatic bile duct epithelial cells. Lab Investig J Tech Methods Pathol 1996; 74:303-13.
9. Alpini G, Ulrich C, Roberts S, Phillips J O, Ueno Y, Podila P V, et al. Molecular and functional heterogeneity of cholangiocytes from rat liver after bile duct ligation. Am J Physiol 1997; 272:G289-297.
10. Dianat N, Steichen C, Vallier L, Weber A, Dubart-Kupperschmitt A. Human pluripotent stem cells for modelling human liver diseases and cell therapy. Curr Gene Ther 2013; 13:120-32.
11. Touboul T, Hannan NRF, Corbineau S, Martinez A, Martinet C, Branchereau S, et al. Generation of functional hepatocytes from human embryonic stem cells under chemically defined conditions that recapitulate liver development. Hepatology 2010; 51:1754-65.
12. Yang G, Si-Tayeb K, Corbineau S, Vernet R, Gayon R, Dianat N, et al. Integration-deficient lentivectors: an effective strategy to purify and differentiate human embryonic stem cell-derived hepatic progenitors. BMC Biol 2013; 11:86.
13. Cerec V, Glaise D, Gamier D, Morosan S, Turlin B, Drenou B, et al. Transdifferentiation of hepatocyte-like cells from the human hepatoma HepaRG cell line through bipotent progenitor. Hepatology 2007; 45:957-67.
14. Gripon P, Rumin S, Urban S, Le Seyec J, Glaise D, Cannie I, et al. Infection of a human hepatoma cell line by hepatitis B virus. Proc Natl Acad Sci USA 2002; 99:15655-60.
15. Krupczak-Hollis K, Wang X, Kalinichenko V V, Gusarova G A, Wang I-C, Dennewitz M B, et al. The mouse Forkhead Box ml transcription factor is essential for hepatoblast mitosis and development of intrahepatic bile ducts and vessels during liver morphogenesis. Dev Biol 2004; 276:74-88.
16. Alvaro D, Metalli V D, Alpini G, Onori P, Franchitto A, Barbaro B, et al. The intrahepatic biliary epithelium is a target of the growth hormone/insulin-like growth factor 1 axis. J Hepatol 2005; 43:875-83.
17. Yokomuro S, Tsuji H, Lunz J G, Sakamoto T, Ezure T, Murase N, et al. Growth control of human biliary epithelial cells by interleukin 6, hepatocyte growth factor, transforming growth factorβ1, and activin a: Comparison of a cholangiocarcinoma cell line with primary cultures of non-neoplastic biliary epithelial cells. Hepatology 2000; 32:26-35.
18. Rastegar M, Lemaigre F P, Rousseau G G. Control of gene expression by growth hormone in liver: key role of a network of transcription factors. Mol Cell Endocrinol 2000; 164:1-4.
19. Mackey S L, Darlington G J. CCAAT enhancer-binding protein alpha is required for interleukin-6 receptor alpha signaling in newborn hepatocytes. J Biol Chem 2004; 279:16206-13.
20. Ahmed T A, Buzzelli M D, Lang C H, Capen J B, Shumate M L, Navaratnarajah M, et al. Interleukin-6 inhibits growth hormone-mediated gene expression in hepatocytes. Am J Physiol Gastrointest Liver Physiol 2007; 292:G1793-1803.
21. Alpini G, Ueno Y, Glaser S S, Marzioni M, Phinizy J L, Francis H, et al. Bile acid feeding increased proliferative activity and apical bile acid transporter expression in both small and large rat cholangiocytes. Hepatology 2001; 34:868-76.
22. Hattoum A, Rubin E, Orr A, Michalopoulos G K. Expression of hepatocyte epidermal growth factor receptor, FAS and glypican 3 in EpCAM-positive regenerative clusters of hepatocytes, cholangiocytes, and progenitor cells in human liver failure. Hum Pathol 2013; 44:743-9.
23. Pritchett J, Harvey E, Athwal V, Berry A, Rowe C, Oakley F, et al. Osteopontin is a novel downstream target of SOX9 with diagnostic implications for progression of liver fibrosis in humans. Hepatology 2012; 56:1108-16.
24. Huang B Q, Masyuk T V, Muff M A, Tietz P S, Masyuk A I, Larusso N F. Isolation and characterization of cholangiocyte primary cilia. Am J Physiol Gastrointest Liver Physiol 2006; 291:G500-509.
25. Cassiman D, Libbrecht L, Sinelli N, Desmet V, Denef C, Roskams T. The vagal nerve stimulates activation of the hepatic progenitor cell compartment via muscarinic acetylcholine receptor type 3. Am J Pathol 2002; 161:521-30.
26. Reynaert H, Rombouts K, Vandermonde A, Urbain D, Kumar U, Bioulac-Sage P, et al. Expression of somatostatin receptors in normal and cirrhotic human liver and in hepatocellular carcinoma. Gut 2004; 53:1180-9.
27. Shibao K, Hirata K, Robert M E, Nathanson M H. Loss of inositol 1,4,5-trisphosphate receptors from bile duct epithelia is a common event in cholestasis. Gastroenterology 2003; 125:1175-87.
28. Blouin M J, Lamy I, Loranger A, Noel M, Corlu A, Guguen-Guillouzo C, et al. Specialization Switch in Differentiating Embryonic Rat Liver Progenitor Cells in Response to Sodium Butyrate. Exp Cell Res 1995; 217: 22-30.
29. Andersen J B, Factor V M, Marquardt J U, Raggi C, Lee Y-H, Seo D, et al. An integrated genomic and epigenomic approach predicts therapeutic response to zebularine in human liver cancer. Sci Transl Med 2010; 2:54ra77.
30. Sia D, Hoshida Y, Villanueva A, Roayaie S, Ferrer J, Tabak B, et al. Integrative molecular analysis of intrahepatic cholangiocarcinoma reveals 2 classes that have different outcomes. Gastroenterology 2013; 144:829-40.
31. Alvaro D, Alpini G, Onori P, Franchitto A, Glaser S S, Le Sage G, et al. Alfa and beta estrogen receptors and the biliary tree. Mol Cell Endocrinol 2002; 193:105-8.
32. Steichen C, Luce E, Maluenda J, Tosca L, Moreno-Gimeno I, Desterke C, et al. Messenger RNA-versus retrovirus-based iPSC reprogramming strategies: analysis of genomic integrity. Stem Cells Transl Med in press.

33. Ros J E, Libbrecht L, Geuken M, Jansen PLM, Roskams TAD. High expression of MDR1, MRP1, and MRP3 in the hepatic progenitor cell compartment and hepatocytes in severe human liver disease. J Pathol 2003; 200:553-60.
34. Lemaigre F P. Molecular mechanisms of biliary development. Prog Mol Biol Transl Sci 2010; 97:103-26.
35. Firrincieli D, Zaiga S, Rey C, Wendum D, Lasnier E, Rainteau D, et al. Vitamin D nuclear receptor deficiency promotes cholestatic liver injury by disruption of biliary epithelial cell junctions in mice: Hepatology. Hepatology 2013; 58:1401-12.
36. Xia X, Jung D, Webb P, Zhang A, Zhang B, Li L, et al. Liver X receptor β and peroxisome proliferator-activated receptor δ regulate cholesterol transport in murine cholangiocytes. Hepatology 2012; 56:2288-96.
37. Chen X-M, Splinter P L, O'Hara S P, LaRusso N F. A Cellular Micro-RNA, let-7i, Regulates Toll-like Receptor 4 Expression and Contributes to Cholangiocyte Immune Responses against *Cryptosporidium parvum* Infection. J Biol Chem 2007; 282:28929-38.
38. Roskams T A, Theise N D, Balabaud C, Bhagat G, Bhathal P S, Bioulac-Sage P, et al. Nomenclature of the finer branches of the biliary tree: canals, ductules, and ductular reactions in human livers. Hepatology 2004; 39:1739-45.
39. Glaser S, Francis H, Demorrow S, Lesage G, Fava G, Marzioni M, et al. Heterogeneity of the intrahepatic biliary epithelium. World J Gastroenterol WJG 2006; 12:3523-36.
40. Péan N, Doignon I, Garcin I, Besnard A, Julien B, Liu B, et al. The receptor TGR5 protects the liver from bile acid overload during liver regeneration in mice: Hepatology. Hepatology 2013; 58:1451-60.
41. Lagoudakis L, Garcin I, Julien B, Nahum K, Gomes D A, Combettes L, et al. Cytosolic calcium regulates liver regeneration in the rat. Hepatology 2010; 52:602-11.
42. Debnath J, Muthuswamy S K, Brugge J S. Morphogenesis and oncogenesis of MCF-10A mammary epithelial acini grown in three-dimensional basement membrane cultures. Methods 2003; 30:256-68.
43. Sirbu A, Ruskin H J, Crane M. Cross-platform microarray data normalisation for regulatory network inference. PloS One 2010; 5:e13822.
44. Tibshirani R, Hastie T, Narasimhan B, Chu G. Diagnosis of multiple cancer types by shrunken centroids of gene expression. Proc Natl Acad Sci USA 2002; 99:6567-72.
45. Taminau J, Meganck S, Lazar C, Steenhoff D, Coletta A, Molter C, et al. Unlocking the potential of publicly available microarray data using inSilicoDb and inSilicoMerging R/Bioconductor packages. BMC Bioinformatics 2012; 13:335.
46. Strazzabosco M l, Somlo S. Polycystic liver diseases: congenital disorders of cholangiocyte signaling; Gastroenterology. 2011 June; 140(7): 1855-9

The invention claimed is:

1. A method for inducing human cholangiocyte differentiation comprising the steps of:
(i) providing a population of human hepatoblasts (hHB); and
(ii) culturing the population of hHB in at least one cholangiocyte induction medium to specifically induce cholangiocyte differentiation and produce a population of cholangiocytes, wherein the step (ii) comprises the steps of:
(a) culturing the population of hHB in a first cholangiocyte induction medium, wherein said first cholangiocyte induction medium is a chemically defined medium (CDM) comprising both growth hormone (GH) and epidemal growth factor (EGF), without human interleukin-6 or a variant thereof, and without sodium taurocholate hydrate or sodium butyrate;
(b) further culturing the population of hHB produced in step (a) in a second cholangiocyte induction medium according to step (ii), wherein said second cholangiocyte induction medium is the CDM of step (ii) to which is added human interleukin-6 (IL-6) or a variant thereof having at least 90% amino acid identity to the human IL-6 and at least 90% of the activity of the human IL-6; and
(c) further culturing the population of hHB produced in step (b) in a third cholangiocyte induction medium, wherein said third cholangiocyte induction medium is a CDM of step (a) to which is added sodium taurocholate hydrate and optionally sodium butyrate,
wherein steps (a), (b) and (c) are performed sequentially (a) to (c),
and
wherein at least 60% of differentiated cells produced in step (ii) are cholangiocytes.

2. The method of claim 1, wherein the population of hHB is cultured for at least 3 days in each of steps (a) to (c).

3. The method of claim 1, wherein the step (b) comprises the steps of: (x) culturing for 3 days the population of hHB in the second cholangiocyte induction medium which has human interleukin-6 (IL-6) or a variant thereof having at least 90% amino acid identity to the human IL-6, and having at least 90% of the activity of the human IL-6; (y) further passaging the population of hHB at least one time; and (z) further culturing the population of hHB for another 3 days in the second cholangiocyte induction medium which has IL-6 activity.

4. The method of claim 1, wherein the population of hHB has been passaged at least one time before culturing the population in a cholangiocyte induction medium.

5. The method of claim 1 wherein the population of hHB is derived from a population of human pluripotent stem cells or from HepaRG.

6. The method of any claim 5, wherein the human pluripotent stem cells are embryonic stem cells (hESCs) or induced pluripotent stem cells (hiPSCs).

7. The method of claim 6, wherein the hiPSCs are derived from cells obtained from an individual with a cholangiopathy and the human cholangiocytes that are differentiated from the hiPSCs display a disease phenotype.

8. The method of claim 5, wherein the hHB derived from a population of human pluripotent stem cells is obtained by a method for inducing hepatic differentiation comprising the steps of: (i) providing the population of human pluripotent stem cells; (ii) culturing the population of human pluripotent stem cells in a endoderm induction medium to produce a population of anterior definitive endoderm (ADE) cells, wherein the endoderm induction medium is a CDM comprising WNT3a, LY294002 and Activin A; (iii) culturing the population of ADE cells in a hepatic induction medium to produce a population of specified hepatic endodermal cells, wherein the hepatic induction medium is a CDM comprising FGF2 and BMP4; and (iv) culturing the population of specified hepatic endodermal cells in a hepatic maturation medium to produce a population of hHB, wherein the hepatic maturation medium is a CDM comprising FGF4, hepatic growth factor (HGF), EGF and retinoic acid (RA).

9. The method of claim 8, wherein the human pluripotent stem cells are previously cultured in a medium comprising bovine serum albumin (BSA), FGF2 and Activin A.

10. The method of claim 1, wherein the chemically defined medium (CDM) comprises human IL-6.

11. The method of claim 10, wherein the human IL-6 has an amino acid sequence as shown in Uniprot Accession number P05231 for a full length human IL-6 protein.

12. The method of claim 1, wherein the variant has 100% of the activity of human IL-6.

13. The method of claim 1, wherein at least 70% of differentiated cells are cholangiocytes.

14. The method of claim 1, wherein at least 80% of differentiated cells are cholangiocytes.

15. A method for inducing human cholangiocyte differentiation comprising the steps of:
 (i) providing a population of human hepatoblasts (hHB); and
 (ii) culturing the population of hHB to specifically induce cholangiocyte differentiation and produce a population of cholangiocytes in
  (a) a first cholangiocyte induction medium, wherein said first cholangiocyte induction medium is a CDM comprising both growth hormone (GH) and epidermal growth factor (EGF), without human interleukin-6 or a variant thereof, and without sodium taurocholate hydrate or sodium butyrate;
  (b) further culturing the population of hHB produced in step (a) in a second cholangiocyte induction medium according to step (ii), wherein said second cholangiocyte induction medium is the CDM of step (ii) to which is added human interleukin-6 (IL-6) or a variant thereof having at least 90% amino acid identity to the human IL-6 and at least 90% of the activity of the human IL-6; and
  (c) further culturing the population of hHB produced in step (b) in a third cholangiocyte induction medium, wherein said third cholangiocyte induction medium is a CDM of step (a) to which is added sodium taurocholate hydrate and optionally sodium butyrate,
 wherein steps (a), (b) and (c) are performed sequentially (a) to (c), and
wherein the human IL-6 has an amino acid sequence as shown in Uniprot Accession number P05231 for a full length human IL-6 protein or a variant thereof having at least 90% amino acid identity to human IL-6 and at least 90% of the activity of human IL-6, and
wherein at least 60% of differentiated cells produced in step (ii) are cholangiocytes.

* * * * *